United States Patent [19]
Stern et al.

[11] Patent Number: 6,015,838
[45] Date of Patent: *Jan. 18, 2000

[54] AQUEOUS FILM-FORMING FOAM COMPOSITIONS

[75] Inventors: Richard M. Stern, Woodbury; Wei-Qiang Fan, Cottage Grove, both of Minn.

[73] Assignee: 3M Innovative Properties Company, St. Paul, Minn.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/743,478

[22] Filed: Nov. 4, 1996

[51] Int. Cl.⁷ .............................. B01F 17/00; A62D 1/04
[52] U.S. Cl. .............................. 516/12; 516/915; 252/3; 544/173; 564/147; 564/297
[58] Field of Search .................. 252/3; 544/170, 544/171, 172, 173; 546/245, 250; 564/147, 209, 297; 516/12, 15, 915

[56] References Cited

U.S. PATENT DOCUMENTS

| | | | |
|---|---|---|---|
| 2,519,983 | 8/1950 | Simons | 205/430 |
| 2,567,011 | 9/1951 | Diesslin et al. | 560/227 |
| 2,592,069 | 4/1952 | Reid | 526/245 |
| 2,593,737 | 4/1952 | Diesslin et al. | 562/507 |
| 2,642,416 | 6/1953 | Ahlbrecht et al. | 526/245 |
| 2,647,933 | 8/1953 | Zerte et al. | 570/142 |
| 2,666,797 | 1/1954 | Husted et al. | 568/842 |
| 2,668,864 | 2/1954 | Hals et al. | 570/142 |
| 2,713,593 | 7/1955 | Brice et al. | 562/586 |
| 2,746,997 | 5/1956 | Reid et al. | 570/142 |
| 2,764,602 | 9/1956 | Ahlbrecht | 554/55 |
| 2,764,603 | 9/1956 | Ahlbrecht et al. | 554/55 |
| 2,795,615 | 6/1957 | Husted et al. | 564/510 |
| 2,803,615 | 8/1957 | Ahlbrecht et al. | 252/79 |
| 2,803,656 | 8/1957 | Ahlbrecht et al. | 564/96 |
| 2,809,990 | 10/1957 | Brown | 562/556 |
| 2,950,317 | 8/1960 | Brown et al. | 562/829 |
| 3,088,849 | 5/1963 | Friedlander et al. | 428/422 |
| 3,094,547 | 6/1963 | Heine | 558/175 |
| 3,232,970 | 2/1966 | Hauptschein et al. | 554/103 |
| 3,271,341 | 9/1966 | Garrison, Jr. | 524/777 |
| 3,274,239 | 9/1966 | Selman | 562/503 |
| 3,351,644 | 11/1967 | Hauptschein et al. | 562/851 |
| 3,398,182 | 8/1968 | Guenthner et al. | 558/239 |
| 3,661,776 | 5/1972 | Fletcher et al. | 252/3 |
| 3,721,638 | 3/1973 | Sianesi et al. | 524/758 |
| 3,772,195 | 11/1973 | Francen | 252/8.05 |
| 3,787,351 | 1/1974 | Olson | 523/453 |
| 3,828,085 | 8/1974 | Price et al. | 252/3 |
| 3,896,251 | 7/1975 | Landucci | 442/80 |
| 3,957,657 | 5/1976 | Chiesa, Jr. | 252/3 |
| 4,264,484 | 4/1981 | Patel | 524/168 |
| 4,360,652 | 11/1982 | Dohany | 526/210 |
| 4,555,556 | 11/1985 | Beresniewicz | 526/212 |
| 4,576,869 | 3/1986 | Malholtra | 428/502 |
| 4,749,526 | 6/1988 | Flynn | 562/849 |
| 5,085,786 | 2/1992 | Alm et al. | 252/8.05 |
| 5,144,469 | 9/1992 | Stern et al. | 562/556 |
| 5,266,639 | 11/1993 | Chapman, Jr. et al. | 525/200 |
| 5,362,919 | 11/1994 | Costello et al. | 568/601 |
| 5,488,142 | 1/1996 | Fall et al. | 560/227 |
| 5,506,309 | 4/1996 | Bierschenk et al. | 525/410 |
| 5,539,059 | 7/1996 | Bierschenk et al. | 525/331.6 |
| 5,756,000 | 5/1998 | Hansen et al. | 252/3 |

FOREIGN PATENT DOCUMENTS

| | | | |
|---|---|---|---|
| 0 267 828 | 5/1988 | European Pat. Off. | C07C 53/21 |
| 0 375 610 | 6/1990 | European Pat. Off. | C07H 15/14 |
| 2 015 296 | 4/1970 | France | C08F 1/00 |
| 1 216 116 | 5/1966 | Germany . | |
| 1 812 531 | 6/1970 | Germany | A62D 1/00 |
| 1632714 | 3/1991 | U.S.S.R. . | |
| 1092141 | 11/1967 | United Kingdom | C07C 53/34 |
| 1302612 | 1/1973 | United Kingdom | C07C 135/02 |

OTHER PUBLICATIONS

Database WPIDS on STN, week 9206, London: Derwent Publ., Inc., AN 92–046595, Class E16, SU 1632714 A1 (Voitovich et al.) abstract, 1992.

Yuminov et al. "New Fluorine–Containing Emulsifiers," *International Polymer & Science Technology*, vol. 6, No. 3, pp. 106–109 (1979).

Gambaretto et al., "Perfluorinated Alyphatc α–Akyl Substituted Acids," *La Chemica e l'Industria*, month unknown 1971, vol. 53, pp. 1033–1038.

Abe et al., "The Electrochemical Fluorination of α–Alkyl–Substituted Carboxylic Acids," *Journal of Fluorine Chemistry*, 1978, month unknown vol. 12, pp. 1–25.

Abe et al., "Preparation, Properties, and Industrial Applications of Organofluorine Compounds" Chpt. 1, Ellis Horwood Ltd., Holsted Press (1982) month unknown pp. 19–43.

Abe et al., "Synthesis of Perfluorobicyclic Ethers," *Journal of Fluorine Chemistry*, 1983, month unknown vol. 23, pp.123–146.

LaZerte et al., "Pyrolyses of the Salts of the Perfluoro Carboxylic Acids," *Journal of American Chemical Society*, 1953, month unknown vol. 75, pp. 4525–4528.

Goecke–Flora et al., "Influence of Carbon Chain Length on the Hepatic Effects of Perfluorinated Fatty Acids," *Chem. Res. Toxicol.* 1996, month unknown vol. 9, pp. 689–695.

Nagase, "Electrochemical Fluorination," *Fluorine Chemistry Reviews*, 1967, month unknown vol. 1, pp. 77–106.

*Fluorine Chemistry*, edited by J.H. Simons, Academic Press, Inc., New York, N.Y., 1950, month unknown pp. 416–419.

*Primary Examiner*—Richard D. Lovering
*Assistant Examiner*—Daniel S. Metzmaier
*Attorney, Agent, or Firm*—Kent S. Kokko

[57] ABSTRACT

This invention provides aqueous film-forming foamable (AFFF) compositions comprising one or more environmentally-friendly α-branched fluoroalkylcarbonyl group-containing surfactants.

5 Claims, No Drawings

AQUEOUS FILM-FORMING FOAM COMPOSITIONS

FIELD OF THE INVENTION

This invention relates to α-branched fluoroalkylcarbonyl fluoride compositions, their preparation, and their use. In another aspect, this invention relates to the use of α-branched fluoroalkylcarbonyl fluoride compositions to prepare α-branched fluoroalkylcarbonyl group-containing compositions. In yet another aspect, it relates to intermediates, monomers, repellent treatments and coatings, surfactants, emulsifiers, and aqueous film-forming foamable solutions.

BACKGROUND OF THE INVENTION

Classes of perfluoralkylcarbonyl fluorides containing straight chain perfluoroalkyl groups, cyclic perfluoroalkyl groups, and derivatives thereof are known. U.S. Pat. No. 2,567,011 (Diesslin et al.), for example, describes fluorocarbon carbonyl fluorides, monocarboxylic acids, and their derivatives containing open-chain (i.e., non-cyclic) and closed-chain (i.e., cyclic) perfluoroalkyl groups, and combinations of cyclic and non-cyclic fluorinated alkyl subradicals. All open chain structures cited by Diesslin et al. are straight chain structures (e.g., $CF_3(CF_2)_n$—); no branched open chain structures are noted.

U.S. Pat. No. 3,351,644 (Hauptschein et al.) describes straight-chain telomeric acid fluorides of the structure $R_f(CF_2CF_2)_nCOF$, where $R_f$ is a perfluoroalkyl or monochloroperfluoroalkyl group and where n is a small number from 1 to about 8.

British Amended Patent 1,092,141 describes perfluoroalkylcarbonyl fluorides containing omega (ω)-branched perfluoroalkyl chains, i.e. of the structure $(CF_3)_2CF(CF_2)_n$—. These ω-branched perfluoroalkylcarbonyl fluorides reportedly are produced as a minor component during electrochemical fluorination of straight chain hydrocarbon carbonyl fluorides and derivatives.

U.S. Pat. No. 4,749,526 (Flynn) describes α-branched perfluoropolyether carbonyl fluorides having the general formula $R_fCF_2O[CF(CF_3)CF_2O]_pCF(CF_3)COF$. Acids derived from these materials have been shown to be stable to decarboxylation of the perfluoropolyether chain.

Short-chain α-branched perfluoroalkylcarbonyl fluorides and acids and certain classes of short-chain cyclic group-containing α-branched perfluoroalkylcarbonyl fluorides are known. Gambaretto et al. (*Chim. Ind.*, 1971, 53, 1033–8) reports the preparation of $C_4F_9CF(C_2F_5)CO_2H$ and $(CF_3)_2CFCO_2H$ by electrochemical fluorination and the subsequent decarboxylation of these acids. The electrochemical fluorination of α-alkyl-substituted acid chlorides and methyl esters to give perfluorooxolanes and perfluorooxanes as well as a small amount, i.e. nine percent, of the corresponding perfluoroalkanoyl fluorides (e.g. $C_5F_{11}CF(CF_3)COF$) also has been reported. (Abe, T. et al., *J. Fluorine Chem.*, 1978, 12, 1–25). In this article, Abe et al. also reports the existence of $C_4F_9CF(C_4F_9)COF$.

Certain cycloalkyl group-terminated α-branched perfluoroalkylcarbonyl halides are known. c-$C_6F_{11}CF_2CF(CF_3)$COF has been reported (T. Abe et al. in Chapter 1 of "Preparation, Properties, and Industrial Applications of Organofluorine Compounds," R. E. Banks, editor, Ellis Horwood Ltd., Holsted Press (1982)), and c-$C_5F_9CF(CF_3)$COF and c-$C_5F_9CF(C_2F_5)$COCl (Abe, T. et al., *J Fluorine Chem.*, 1983, 23, 123–146) have been disclosed.

Straight-chained perfluorocarboxylic acids of the structure $R_fCF_2COOH$ and derivatives thereof are known not to degrade under aqueous environmental exposure and do not thermally decarboxylate until at least 180–200° C. (*J. Am. Chem. Soc.*, 1953, 75, 4525–28). These compounds are very stable and, therefore, also persist in the environment. It is also known that linear perfluorocarboxylic acids and their carboxylate salts are moderately toxic, especially longer chain salts such as n-$C_9F_{19}COO^-NH_4^+$. (See, e.g., Goeche-Flora et al., *Chem. Res. Toxicol.* 1996, 9, 689–95).

While it is known that fluorochemical acids of the type $(R_f)_2CFCO_2H$, where $R_f$ is a short chain such as $CF_3$ and $C_2F_5$, are unstable in aqueous solution (See, e.g., *Chim. Ind.*, 1971, 53, 1033–8), these compounds generally possess poor surfactant properties.

There are no known fluoroalkylcarbonyl fluoride derivatives that exhibit a combination of those properties that are favorable in today's chemical market. A highly desirable fluorochemical compound is one having superior surfactant properties when dissolved in a liquid (i.e., can reduce the surface tension of the liquid to a value lower than 20 dynes/cm), is relatively non-toxic or is very low in toxicity, and is non-persistent in the environment (i.e., can completely degrade biochemically, thermally, or photochemically under mild conditions such as those encountered in the environment under ambient conditions).

SUMMARY OF THE INVENTION

Briefly, in one aspect, the present invention provides compositions of open-chain, α-branched fluoroalkylcarbonyl fluorides, and derivatives thereof, that can be represented generally by the formula:

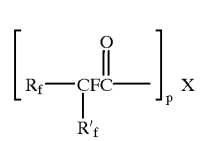

wherein:

$R_f$ and $R'_f$ are selected independently from one another as a fluorinated, preferably perfluorinated, group bonded through carbon that may be substituted or unsubstituted, cyclic or acyclic, linear or branched (or any combination thereof) and may optionally contain one or more catenary heteroatoms such as nitrogen, sulfur, or oxygen; $R_f$ or $R'_f$ may contain one or more hydrogen atoms or one or more other halogen atoms, e.g. chlorine, provided that at least 75%, and preferably at least 90%, of the atoms attached to the carbon backbone are fluorine atoms;

p may be 1, 2, several or many, equalling the valency of X;

X is halogen, a hydroxyl group, or a moiety remaining after the reaction of an α-branched fluoroalkylcarbonyl fluoride with a reagent containing at least one active (i.e., acidic) hydrogen atom and after the elimination of hydrogen fluoride; and when X is fluorine or is a hydroxyl group, p is equal to 1, $R_f$ and $R'_f$ are acyclic alkyl groups, at least one of said $R_f$ and $R'_f$ contains at least 5 carbon atoms, and the sum of the carbon atoms in said $R_f$ and $R'_f$ groups is greater than or equal to 7, preferably less than or equal to about 24; preferably the ratio of carbon atoms in said $R_f$ and $R'_f$ moieties is at least 2 to 1.

In another aspect, the present invention provides α-branched fluoroalkylcarbonyl group-containing compounds including derivatives of those compounds depicted by Formula I supra. Such derivatives find utility, for example, as surfactants and emulsifiers and as soil, water, and oil-repellent compositions. In yet another aspect, this invention provides aqueous film-forming foamable (AFFF) compositions comprising one or more a-branched fluoroalkylcarbonyl group-containing surfactants.

The α-branched fluoroalkylcarbonyl derivatives of this invention are environmentally non-persistent and are much lower in toxicity than their linear and cyclic homologues. The α-branched fluoroalkylcarboxylate salt compositions provided herein are very low in toxicity, thermally degrade quickly at temperatures between about 80° C. and about 100° C. in aqueous media, and break down in the environment to volatile, non-surface active species that are eliminated from the body of a transpiring organism.

DETAILED DESCRIPTION OF PREFERRED EMBODIMENTS

In one aspect, this invention provides α-branched fluoroalkylcarbonyl fluorides. A preferred class of these compounds may be represented generally by the following formula.

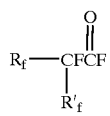

II wherein:
  $R_f$ and $R'_f$ are selected independently from one another as an acyclic fluorinated, preferably perfluorinated, group bonded through carbon that may be substituted or unsubstituted, linear or branched (or any combination thereof) and may optionally contain one or more catenary heteroatoms such as nitrogen, sulfur, or oxygen; $R_f$ or $R'_f$ may contain one or more hydrogen atoms or one or more other halogen atoms, e.g. chlorine, provided that at least 75%, and preferably at least 90%, of the atoms attached to the carbon backbone are fluorine atoms;
  wherein at least one of said $R_f$ and $R'_f$ groups contain at least 5 carbon atoms and wherein the sum of the carbon atoms in said $R_f$ and $R'_f$ moieties is greater than or equal to 7, and preferably less than or equal to about 24; preferably the ratio of carbon atoms in said $R_f$ and $R'_f$ moieties is at least 2 to 1.

An especially preferred class of fluorinated x-substituted carbonyl fluorides can be represented by Formula III:

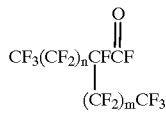

III wherein:
  n is between 5 and about 18 inclusive; and
  m is between 0 and about 9 inclusive where preferably n and m are chosen such that the ratio of (n+1) to (m+1) is at least 2 to 1.

Generally, α-branched fluoroalkylcarbonyl fluorides, such as those depicted above by Formulas II and III, may be prepared through fluorination of a non-fluorinated organic analogue (e.g., an alkylcarbonyl halide or an alkylcarbonyl ester). The fluorination reaction may be carried out either by electrochemical fluorination ("ECF"), sometimes referred to as the "Simons process," with hydrogen fluoride as described, for example, by U.S. Pat. No. 2,519,983 (Simons), or by direct fluorination with elemental fluorine as described, for example, by U.S. Pat. No. 5,488,142 (Fall et al.), both of whose descriptions are hereby incorporated by reference. Preferably, the reaction is carried out by electrochemical fluorination.

The "Simons process" or the "Simons electrochemical fluorination process" is a known, commercially-practical process for reacting anhydrous HF with certain classes of organic compounds. A typical fluorination reaction using the Simons electrochemical fluorination to produce an α-branched trifluoromethyl perfluoroalkylcarbonyl fluoride is given below:

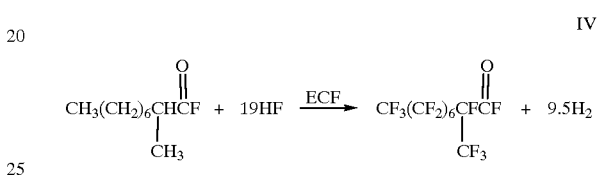

IV

An early patent describing this technology is U.S. Pat. No. 2,519,983 (Simons), which contains a drawing of a Simons cell and its appurtenances, and a description and photograph of laboratory and pilot plant cells appear at pages 416–418 of Vol. 1 of "*Fluorine Chemistry*", edited by J. H. Simons, published in 1950 by Academic Press, Inc., New York. Electrochemical fluorination by the Simons process is also described by S. Nagase in Fluorine Chem. Rev., I (1) 77–106 (1967), and by T. Abe et al. in Chapter 1 of "Preparation, Properties, and Industrial Applications of Organofluorine Compounds," R. E. Banks, editor, Ellis Horwood Ltd., Holsted Press (1982). Other suitable feedstocks which can be electrochemically fluorinated with HF include unsaturated alkylcarbonyl fluorides (e.g., $CH_3(CH_2)_5CH=C(CH_3)COF$), saturated methyl esters (e.g., $CH_3(CH_2)_6CH(CH_3)CO_2CH_3$), and acid chlorides (e.g., $C_7H_{15}CH(CH_3)COCl$).

Generally, in a relatively large-scale setting, a Simons cell useful in the practice of this invention comprises a cell body, typically made of carbon steel and usually provided with a cooling jacket, in which is suspended an electrode pack comprising series of alternating and closely-spaced cathode plates (typically made of iron, nickel, or nickel alloy) and anode plates (typically made of nickel), the plates being immersed in the current-conductive solution of the organic starting material in essentially anhydrous hydrogen fluoride. Gaseous cell effluent comprising the volatilized electrochemically fluorinated product and volatilized hydrogen fluoride can be withdrawn from the cell as an overhead stream via a valved-outlet line. The cell is operated with the conductive solution containing a desired concentration of the organic starting material (the α-branched alkylcarbonyl precursor), typically between 5 and 30 percent, that will result in the production of the desired saturated, fully-fluorinated, or partially-fluorinated product.

The relative temperatures and pressures under which the cell is operated will be those conditions conducive to the production of the desired fluorinated product. Generally, by increasing the concentration of organic starting material in the conductive solution (and thereby decreasing the concentration of the HF reactant), the hydrogen-content of the resulting fluorinated products is increased, the reaction mixture in a sense being "starved" for HF. Generally, the temperature of the cell during the electrochemical fluorination can be in the range of 0° to 70° C., preferably 20° to 60° C. In operation, the cell can be run at a pressure in the range of 760 to 4000 torr, preferably in the range from 1000 to 3000 torr. The cell can be operated at cell voltages in the range of 4 to 9 volts and current densities in the range of 10 to 100, preferably 20 to 80, mAmp/cm$^2$ of active anode surface (where the electrolysis takes place). The cell can be operated either at constant current or constant voltage.

The reactor gaseous effluent, comprising the fluorinated adduct, hydrogen fluoride, hydrogen, and other gaseous products, can be withdrawn from the top of the reactor and passed to a condenser system, as described supra. The fluorination product can be removed from the cell as part of the gaseous effluent. The effluent can be cooled to condense and collect or recover the aforementioned saturated and partially- or fully-fluorinated a-branched fluoroalkylcarbonyl fluorides. Any unreacted HF or by-products can also be condensed and recycled to the cell.

Other details of the Simons electrochemical fluorination process and cell will be omitted here in the interest of brevity, and the disclosure of such technology in the above-cited references to such technology can be referred to for descriptions of such detail, whose descriptions are herein incorporated for such purpose.

α-Branched fluoroalkylcarbonyl fluoride precursors may also be prepared by direct fluorination with excess elemental fluorine using known methods. A typical direct fluorination reaction with elemental fluorine to produce an α-branched fluoroalkylcarbonyl derivative is shown below:

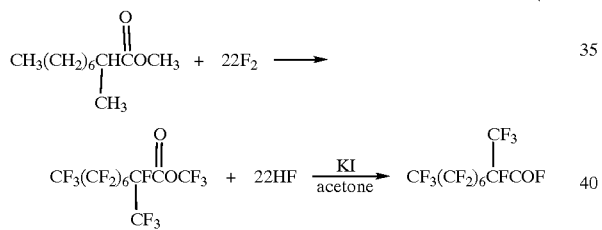

V

Other suitable feedstocks useful in the methods of direct fluorination heretofore described include branched esters (e.g., CH$_3$(CH$_2$)$_6$CH(CH$_3$)CH$_2$OCOCH$_3$) and unsaturated esters (e.g., CH$_3$(CH$_2$)$_5$CH=C(CH$_3$)COOCH$_3$).

U.S. Pat. No. 5,488,142 (Fall et al.), whose description is incorporated herein by reference, describes a useful direct fluorination method. According to this method, a diluted solution of the organic precursor material (typically a short chain alkyl ester of an α-branched carboxylic acid) in a normally liquid, inert medium (e.g., perfluoromethyl morpholine) is directly contacted with a stoichiometric excess of fluorine gas, F$_2$, which preferably is diluted with an inert gas such as nitrogen, in a temperature-controlled, turbulent, tubular flow-style reactor to fluorinate the precursor material at a temperature and a flow rate of inert gas (if used) sufficient to volatilize by-product hydrogen fluoride, HF. The hydrogen fluoride is removed from the reactor as it is produced (and is not recycled) so that the fluorination is substantially carried out in a hydrogen fluoride-free environment. The resultant solution of fluorinated organic substance (typically a perfluorinated short chain alkyl ester of an α-branched carboxylic acid) is then removed from the reactor. The fluorinated product, using this method, can be separated from the inert medium, e.g. by distillation, to obtain the fluorinated product as the product of the process, or, if a fluorinated alkyl ester, can be easily converted to the fluorinated carbonyl fluoride by treatment with potassium iodide in acetone.

Other details of this preferred method of direct fluorination and details of other useful methods of direct fluorination are omitted in the interest of brevity, as those details are well-known and established in the art.

Yields of the α-branched carbonyl derivatives of this invention obtained using electrochemical fluorination typically range from about 20 to about 50 percent (compared to yields of only around 15% with isomeric straight chain carbonyl derivatives), while typical yields using direct fluorination reach as high as 60–80%. The choice of a preferred fluorination method will of course be governed by a combination of any given set of business and technical concerns. Electrochemical fluorination yields of the a-branched compositions taught herein are surprisingly high. One would expect a high degree of degradation or isomerization to linear compounds; yet instead, ECF yields are much improved over yields obtained for linear analogues of the α-branched compositions.

In a second aspect of this invention, derivatives of α-branched fluoroalkylcarbonyl fluorides are provided. Among the many and varied classes of useful derivatives that may be prepared from the α-branched fluoroalkyl carbonyl fluorides described herein are carboxylate salts, ester derivatives (e.g., acrylates and methacrylates), amide derivatives, and dihydrofluoroalkyl derivatives. Classes of oligomers and polymers may also be obtained.

Generally, the most useful α-branched fluoroalkylcarbonyl fluoride derivatives will be those prepared by the reaction of an α-branched fluoroalkylcarbonyl fluoride with a reagent containing at least one active hydrogen atom. Generally, the simplest of these compounds are those that may be represented by the following general Formula VI where a single α-branched fluoroalkylcarbonyl moiety is bonded to the residue of the active hydrogen-containing reagent existing after the elimination of hydrogen fluoride.

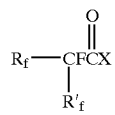

VI wherein:

R$_f$ and R'$_f$ are selected independently from one another as a fluorinated, preferably perfluorinated, group bonded through carbon that may be substituted or unsubstituted, cyclic or acyclic, linear or branched (or any combination thereof) and may optionally contain one or more catenary heteroatoms such as nitrogen, sulfur, or oxygen; R$_f$ or R'$_f$ may contain one or more hydrogen atoms or one or more other halogen atoms, e.g. chlorine, provided that at least 75%, and preferably at least 90%, of the atoms attached to the carbon backbone are fluorine atoms; preferably the ratio of carbon atoms in said R$_f$ and R'$_f$ moieties is at least 2 to 1; and X is chlorine or bromine or is a group of the formula —N(R$^1$)(R$^2$), —OR"$_f$, —YQOR, —YQN(R$^1$)(R$^2$), —YQZ, or —O$^-$ 1/qM$^{q+}$ (q=valency of M) where R"$_f$ is a fluorinated alkyl group and R, R$^1$, and R$^2$ are, independently from one another, selected as hydrogen, or an alkyl, aryl, alkaryl, aralkyl (or any combination thereof) group that may be substituted or unsubstituted, saturated, linear or branched, cyclic or acyclic, and may contain one or more catenary heteroatoms such as oxygen or nitrogen; where present, $R^1$ and $R^2$ together with the depicted nitrogen can form a heterocyclic ring, such as a piperidino or morpholino group; Y is O, S, or NR, where R is as defined supra; Q is a substituted or unsubstituted divalent organic group; M is a cation selected from the group consisting of $H^+$(i.e., the free carboxylic acid), metal cation (e.g., $Na^+$, $K^+$, $Li^+$, $Ca^{2+}$, $Mg^{2+}$, $Fe^{3+}$, $Al^{3+}$ or $Zn^{2+}$), ammonium cation (i.e., $H_4N^+$), substituted ammonium cation (e.g., $H_{1-3}N^+(CH_3)_{3-1}$, $H_{1-3}N^+(C_2H_5)_{3-1}$, $H_{1-3}N^+(C_2H_4OH)_{3-1}$, $(CH_3)_4N^+$ or $(C_4H_9)_4N^+$), and polyammonium cation (e.g., $H_3N^+(C_2H_4NH)_{0-3}C_2H_4N^+H_3$), and Z is an anionic, cationic, nonionic or amphoteric water-solubilizing group (e.g., sulfonate, sulfate, ether sulfate, phosphate, quaternary ammonium, betaine, sulfobetaine or polyoxyethylene) or is an ethylenically unsaturated group (e.g., —OC(O)CH=$CH_2$ and —OC(O)C($CH_3$)=$CH_2$).

A preferred subclass of these α-substituted fluoroalkylcarbonyl fluoride derivatives is that represented below by Formula VII:

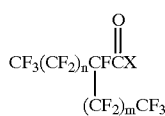

VII wherein:
n is between 4 and about 18 inclusive;
m is between 0 and about 9 inclusive where preferably n and m are chosen such that the ratio of (n+1) to (m+1) is at least 2 to 1; and
X is as described supra by Formula VI.

Acid derivatives of α-substituted fluoroalkylcarbonyl fluorides can be synthesized readily from the α-branched fluoroalkylcarbonyl fluorides. To form the fluoroalkylcarbonyl chloride, the carbonyl fluoride can reacted with hydrazine followed by chlorine using, for example, the procedure described in U.S. Pat. No. 2,950,317 (Brown et al.). Fluorocarboxylic acids may be obtained by reacting the carbonyl fluoride or chloride with water, preferably also in the presence of acid, and the carboxylate salts are most conveniently made by reacting either the carbonyl fluoride or the carboxylic acid with a base, preferably in water. Esters can be made by reacting the carbonyl fluoride or chloride with a primary, secondary, or tertiary alcohol. These reactions involving fluorocarboxylic acids can be run as described in U.S. Pat. No. 2,567,011 (Diesslin et al).

Amides are particularly useful intermediates that can be prepared by reacting the fluoroalkylcarbonyl fluoride with ammonia, a primary amine or a secondary amine. Primary amides may be made as instructed in U.S. Pat. No. 2,567,011. The primary amides can further be derivatized, for example, by reaction with a glycol ester followed by saponification to form carboxylate salts as described, for example, in U.S. Pat. No. 2,809,990 (Brown). Of particular interest is the reaction with N,N-dimethylaminopropyl amine to form the tertiary amidoamine intermediate, which can be prepared as described in U.S. Pat. No. 2,764,603 (Ahlbrecht). The amidoamine can in turn be reacted in a number of ways to form a variety of cationic and amphoteric surfactants: for example, it can be quaternized with an alkyl halide to form a quaternary ammonium salt, as described in U.S. Pat. No. 2,764,602 (Ahlbrecht); it can be oxidized with hydrogen peroxide to form an amine oxide, as described in British Specification 1,302,612; it can be reacted with a chloroalkylcarboxylate salt or a chloroalkylsulfonate salt to form a betaine or a sultaine amphoteric surfactant respectively; it can be reacted with acrylic acid to form the Michael adduct to the amine nitrogen, as described in U.S. Pat. No. 5,144,069 (Stern et al.); or it can be reacted with β-propiolactone to form a carboxyethyl amphoteric surfactant, as described in U.S. Pat. No. 3,661,776 (Fletcher et al.). While esters and amides of linear fluorocarboxylic acids are unstable to hydrolysis, esters and amides of α-branched fluorocarboxylic acids are more stable to hydrolysis.

The fluoroalkylcarbonyl fluoride may also be reacted with aminoalcohols such as (N-methyl)-2-aminoethanol and (N-ethyl)-2-aminoethanol as described in U.S. Pat. No. 2,803,656 (Ahlbrecht et al.), replacing the n-perfluorooctanecarbonyl fluoride of Ahlbrecht's Example 1 with α-branched fluoroalkylcarbonyl fluoride, to produce useful fluorinated amidoalcohols. The resulting amidoalcohols can be ethoxylated (as described for example in U.S. Pat. No. 2,567,011 (Diesslin et al.)), sulfated (as described for example in U.S. Pat. No. 2,803,656 (Ahlbrecht et al.)) or phosphated (as described in U.S. Pat No. 3,094,547 (Heine)) to prepare nonionic or anionic degradable fluoroaliphatic surfactants. Useful oil and water repellent treatments may be produced from these fluorinated amido alcohols: for example, (1) by reaction with acrylic or methacrylic acid or acryloyl or methacryloyl chloride to form an acrylate or methacrylate monomer and then polymerizing or copolymerizing the monomer using a standard free radical initiator to form a repellent polymer (see, e.g., U.S. Pat. No. 2,803,615 (Ahlbrecht et al.); (2) by reaction with isocyanates to form repellent fluoroaliphatic urethanes, ureas, or carbodiimides (see, e.g., U.S. Pat. Nos. 3,398,182 (Guenthner et al.) and 3,896,251 (Landucci)); or (3) by reaction with carboxylic acids (or derivatives thereof) to form repellent esters (see, e.g., U.S. Pat. No. 4,264,484 (Patel)).

Another novel class of compositions provided by this invention are α-branched 1,1-dihydrofluoroalkyl derivatives. Such compositions, which may be prepared by reducing α-branched fluoroalkylcarbonyl fluorides, can be represented by Formula VIII below:

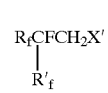

VIII wherein:
$R_f$ and $R'_f$ are selected independently from one another as a fluorinated, preferably perfluorinated, group bonded through carbon that may be substituted or unsubstituted, cyclic or acyclic, linear or branched (or any combination thereof) and may optionally contain one or more catenary heteroatoms such as nitrogen, sulfur, or oxygen; $R_f$ or $R'_f$ may contain one or more hydrogen atoms or one or more other halogen atoms, e.g. chlorine, provided that at least 75%, and preferably at least 90%, of the atoms attached to the carbon backbone are fluorine atoms; preferably the ratio of carbon atoms in said $R_f$ and $R'_f$ moieties is at least 2 to 1; and X' is —OR, —$OSO_2R$, —OCOR, —$N(R^1)(R^2)$, —SR, halogen, or an ethylenically unsaturated moiety (e.g., acrylate, methacrylate, allyl, vinyl ether, vinyl benzyloxy) where R, $R^1$ and $R^2$ are as defined supra in Formula VI.

A preferred class of these above-described α-branched 1,1-dihydrofluoroalkyl derivatives include the 1,1-dihydrofluoroalkyl derivatives represented by Formula IX below:

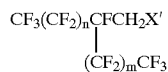

IX wherein:
n is between 4 and about 18 inclusive;
m is between 0 and about 9 inclusive where preferably n and m are chosen such that the ratio of (n+1) to (m+1) is at least 2 to 1; and
X' is as defined supra by Formula VIII.

The α-branched fluoroalkylcarbonyl fluoride derivatives often exhibit superior water solubility, superior surface tension vs. concentration profiles, and critical micelle concentrations (CMCs) that are comparable to their isomeric linear fluoroalkylcarbonyl fluoride derivatives with the same carbon number. Thus, they are excellent candidates as emulsifiers and surfactants in applications where environmental persistence is of concern. Such applications include fluoropolymer emulsions, cleaning solutions, aqueous film-forming foams, coating additives, plating baths, wetting agents, floor polish levelling agents, dispersion aids, oil well stimulation chemicals, and photographic coupling agents. Typically, those α-branched fluoroalkylcarbonyl fluoride derivatives exhibiting the most favorable surface activity characteristics will be those having a long fluorinated alkyl group (i.e., having 5 or more carbon atoms) and a short α-branched alkyl group (i.e., perfluoromethyl or perfluoroethyl).

α-Branched fluoroalkylcarbonyl fluoride derivatives especially preferred as emulsifiers for preparing stable fluoropolymer emulsions, latexes, and suspensions, e.g., polytetrafluoroethylene and polyvinylidene fluoride emulsions, (including those methods described by U.S. Pat. No. 4,360,652 (Dohany), which is incorporated herein by reference) are α-branched fluorocarboxylate salts that may be represented generally by Formula X below.

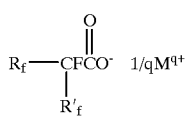

X wherein:
$R_f$ and $R'_f$ are selected independently from one another as a fluorinated, preferably perfluorinated, group bonded through carbon that may be substituted or unsubstituted, cyclic or acyclic, linear or branched (or any combination thereof) and may optionally contain one or more catenary heteroatoms such as nitrogen, sulfur, or oxygen; $R_f$ or $R'_f$ may contain one or more hydrogen atoms or one or more halogen atoms, e.g. chlorine, provided that at least 75%, and preferably at least 90%, of the atoms attached to the carbon backbone are fluorine atoms; preferably the ratio of carbon atoms in said $R_f$ and $R'_f$ moieties is at least 2 to 1;

M is a cation selected from the group consisting of $H^+$ (i.e., the free carboxylic acid), metal cation (e.g., $Na^+$, $K^+$, $Li^+$, $Ca^{2+}$, $Mg^{2+}$, $Fe^{3+}$, $Al^{3+}$ or $Zn^{2+}$), ammonium cation (i.e., $H_4N^+$), substituted ammonium cation (e.g., $H_{1-3}N^+(CH_3)_{3-1}$, $H_{1-3}N+(C_2H_5)_{3-1}$, $H_{1-3}N^+(C_2H_4OH)_{3-1}$, $(CH_3)_4N^+$ or $(C_4H_9)_4N^+$), and polyammonium cation (e.g., $H_3N^+(C_2H_4NH)_{0-3}C_2H_4N^+H_3$); and q is equal to the valency of M.

A preferred class of these above-described α-branched fluorocarboxylate salts is that represented by Formula XI below:

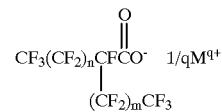

XI wherein:
n is between 4 and about 18 inclusive;
m is between 0 and about 9 inclusive where preferably n and m are chosen such that the ratio of (n+1) to (m+1) is at least 2 to 1; and
M and q are as defined supra by Formula X.

In their dry state, the α-branched fluorocarboxylate salts decarboxylate at temperatures of approximately 140–190° C. to form mostly internal fluoroolefins such as depicted below for an exemplary species:

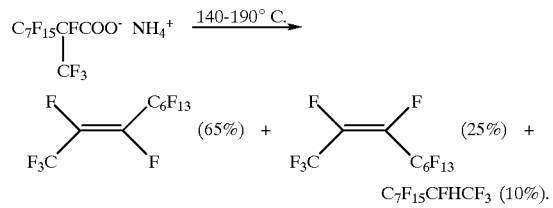

$C_7F_{15}CFHCF_3$ (10%).

The straight chain isomers (also in dry state) decompose at a slightly higher temperature of approximately 180–200° C. in a sealed tube to form terminal fluoroolefins:

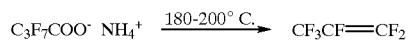

(J. Am. Chem. Soc., 1953, 75, 4525-28).

In aqueous solution the α-branched fluorocarboxylate salts readily undergo decarboxylation at temperatures of 60–100° C. or lower to give a mixture consisting of roughly 85% monohydride and 15% olefin, isolatable and recoverable by azeotropic distillation. The straight chain isomers, however, will not decompose in water at a temperature of less than 100° C. (e.g., in refluxing water). In water, the pH and the initial concentration of the a-branched salts also greatly affect the rate of thermal decarboxylation, as the decarboxylation reaction slows in more acidic aqueous solution or at higher emulsifier concentration. Changing the nature of the cation, e.g., from sodium to ammonium, does not, however, greatly affect the rate of thermal degradation in the environment.

While not wanting to be held to any particular theory, it is believed that the degradation of α-branched fluorocarboxylic acids and their derivatives occurs via the decarboxylation of the α-branched fluorocarboxylate anion (often created from hydrolysis and/or oxidation) to form volatile, non-atmospherically-persistent fluorocarbon species, such as olefins and monohydrides. The carboxylate anion can be formed from hydrolysis and/or oxidation of other α-branched derivatives. If ingested by a transpiring organism, the a-branched fluorocarboxylic acids and their derivatives degrade to the above-mentioned volatile materials that are readily eliminated from the body, unlike their linear acid analogs which are retained unchanged in the body for long periods of time. Organisms will also promote the degradation of α-branched materials to volatile materials that are readily eliminated by the organism. As the degradation mechanism appears to be independent of a biochemical mechanism, degradation and elimination should occur in all transpiring organisms (rodents and primates). The salts of α-branched fluorocarboxylic acids cannot therefore persist indefinitely in the body of the organism as do some of their linear analogs. The esters and amides of α-branched fluorocarboxylic acids are, however, much more hydrolytically stable than their linear analogues.

Removal and recycling of fluorinated emulsifiers from fluoropolymer water emulsions during emulsion polymerization processes have become critical from environmental, economic, and performance standpoints. α-Branched fluorocarboxylic acid ammonium salts are particularly useful as such fluorinated emulsifiers. Generally in practice of emulsion polymerization, the emulsifier and free radical initiator are first added to water following which is added the fluoromonomers as is described in more detail by U.S. Pat. 4,576,869 (Malholtra), whose description is incorporated herein by reference. Typically utilized free radical initiators include diisopropyl peroxydicarbonate and permanganate compounds of the formula $XMnO_4$ where X is hydrogen, ammonium, alkali earth metal, or alkaline earth metal. One or more chain transfer agents, such as isopropyl alcohol, may also be used to control the molecular weight of the polymer. Useful fluoromonomers include any ethylenically-unsaturated fluorinated compounds such as, for example, tetrafluoroethylene, vinylidene fluoride, trifluoroethylene, chlorotrifluoroethylene, hexafluoropropene, vinyl fluoride, and pentafluoropropene. Polymerization may be effected by mixing the foregoing ingredients in aqueous media at a temperature typically between about 50 and 125° C. and a pressure typically between about 15 and 40 kg/cm² and generally is carried out in a gently stirred autoclave. Other details of emulsion polymerization techniques will be omitted in the interest of brevity, as such details are well documented and understood in the art and reference may be made to the cited documents for such teaching. After the fluoropolymer polymerization is complete, the α-branched ammonium salt can be easily destroyed by simple azeotropic distillation to give the volatile monohydride and fluoroolefin as product, which can be recovered and derivatized for other applications.

According to recent tests, the salts of a-branched fluorocarboxylic acids have acute toxicities an order of magnitude less (i.e. $LD_{50}$ levels are ten times higher) than the linear (non α-branched) analogues. For instance, the linear long chain ammonium carboxylate salt, $C_9F_{19}COO^-NH_4^+$, is moderately toxic, where its α-branched isomer, $C_7F_{15}CF(CF_3)COO^-NH_4^+$, exhibits relatively low toxicity.

Another class of preferred (x-substituted fluoroalkylcarbonyl fluoride derivatives are tertiary amidoamine intermediates that are useful in the preparation of degradable fluoroaliphatic surfactants. This class of compositions may be represented generally by Formula XII below.

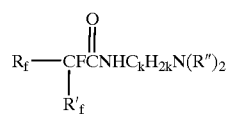

XII wherein:
$R_f$ and $R'_f$ are selected independently from one another as a fluorinated, preferably perfluorinated, group bonded through carbon that may be substituted or unsubstituted, cyclic or acyclic, linear or branched (or any combination thereof) and may optionally contain one or more catenary heteroatoms such as nitrogen, sulfur, or oxygen; $R_f$ or $R'_f$ may contain one or more hydrogen atoms or one or more other halogen atoms, e.g. chlorine, provided that at least 75%, and preferably at least 90%, of the atoms attached to the carbon backbone are fluorine atoms; preferably the ratio of carbon atoms in said $R_f$ and $R'_f$ moieties is at least 2 to 1;

k is between 2 and 6; and

R" is a lower alkyl group having from 1 to 4 carbon atoms, preferably methyl, or $N(R")_2$ may be a heterocyclic ring (such as a pyridyl, piperidino, or morpholino group).

A preferred class of these above-described a-branched tertiary amidoamine intermediates is that represented by Formula XIII below:

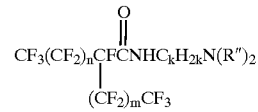

XIII wherein:
k and R" are as defined supra by Formula XII;
n is between 4 and about 18 inclusive, and
m is between 0 and about 9 inclusive where preferably n and m are chosen such that the ratio of (n+1) to (m+1) is at least 2 to 1.

The amidoamine intermediates depicted by Formula XIII supra may subsequently: (1) be either protonated with an inorganic halogen acid (e.g., HCl or HBr), a sulfur-containing inorganic acid (e.g., sulfuric acid), an organic carboxylic acid (e.g., $CH_3COOH$), or an organic sulfonic acid (e.g., benzene sulfonic acid) or be quaternized with an alkylating agent (e.g., an alkyl halide, dialkyl sulfate, or alkyl sulfonate) to form a cationic fluoroaliphatic surfactant; (2) be reacted with a sultone (e.g., gamma-propane sultone), a lactone (e.g., gamma-butyrolactone), an acrylic acid (e.g. acrylic acid), a sulfonato-functional acrylamide (e.g., N-(3-sulfo-2,2-dimethylpropyl)acrylamide) or a similar compound to form an amphoteric zwitterionic fluoroaliphatic surfactant; or (3) be reacted with an oxidizing agent (e.g., hydrogen peroxide) to form the most preferred amphoteric amine oxide surfactant. The details of such reactions are well-known and established in the art.

Some pyridinium oxides and pyridinium salts with ester linkages are similarly prepared from the fluoroalkylcarbonyl fluorides by reaction with for instance 2-(2-hydroxyethyl) pyridine or N-(2-hydroxyethyl)isonicotinamide.

Among the many classes of surfactants that can be so prepared are tertiary amidoamine oxide surfactants and quaternary ammonium surfactants. Preferred members of the former class include those according to Formula XIV below.

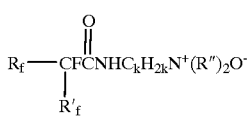
XIV wherein:

$R_f$, $R'_f$, k, and R", are as defined supra by Formula XII.

Preferred quaternary ammonium surfactants can be represented by Formula XV below.

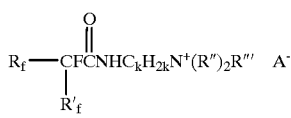
XV wherein:

$R_f$, $R'_f$, k, and R" are as defined sierra by Formula XII;

R'" is hydrogen or a substituted or unsubstituted monovalent organic group; and $A^-$ is an anion which is the residue of the alkylating agent R'"A or the acid HA.

Preferred amphoteric surfactants which can be prepared from α-branched tertiary amidoamine intermediates are those isomers represented by Formulas XVI and XVII below:

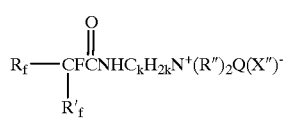
XVI

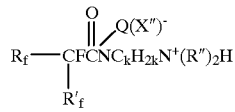
XVII wherein:

$R_f$, $R'_f$, k, and R" are as defined supra by Formula XII;

Q is as defined supra by Formula VI; and

X" is either —$SO_3$ or —COO.

Examples of α-branched fluoroalkylcarbonyl fluorides and derivatives of this invention are given below. The $R_f$— group ($C_nF_{2n+1}$—) group in each formula is primarily normal (i.e., unbranched).

Carbonyl Fluorides $C_6F_{13}CF(CF_3)COF$
$C_6F_{13}CF(C_2F_5)COF$
$C_6F_{13}CF(C_3F_7)COF$
$C_7F_{15}CF(CF_3)COF$
$C_7F_{15}CF(C_2F_5)COF$
$C_7F_{15}CF(C_3F_7)COF$
$C_8F_{17}CF(CF_3)COF$
$C_{10}F_{21}CF(CF_3)COF$
$C_4F_9CF(C_2F_5)COF$
$C_6F_{13}CF(C_4F_9)COF$
$C_6F_{13}CF(C_6F_{13})COF$
$C_{10}F_{21}CF(C_{10}F_{21})COF$
$CF_3CF(CF_3)CF_2CF(CF_3)COF$
$C_{16}F_{33}CF(CF_3)COF$ Acids and Salts

| | |
|---|---|
| $C_5F_{11}CF(CF_3)COO^-\ H_4N^+$ | $C_5F_{11}CF(CF_3)COOH$ |
| $C_5F_{11}CF(CF_3)COO^-\ K^+$ | $C_6F_{13}CF(CF_3)COOH$ |
| $C_6F_{13}CF(CF_3)COO^-\ H_4N^+$ | $C_7F_{15}CF(CF_3)COOH$ |
| $C_6F_{13}CF(CF_3)COO^-\ K^+$ | $C_8F_{17}CF(CF_3)COOH$ |
| $C_6F_{13}CF(CF_3)COO^-\ Na^+$ | $C_{10}F_{21}CF(CF_3)COOH$ |
| $C_7F_{15}CF(CF_3)COO^-\ H_4N^+$ | $C_6F_{13}CF(C_2F_5)COOH$ |
| $C_7F_{15}CF(CF_3)COO^-\ H_3N^+CH_2CH_2OH$ | $C_7F_{15}CF(C_3F_7)COOH$ |
| $C_7F_{15}CF(CF_3)COO^-\ K^+$ | |
| $C_7F_{15}CF(CF_3)COO^-\ Na^+$ | |
| $C_7F_{15}CF(CF_3)COO^-\ Li^+$ | |
| $C_7F_{15}CF(CF_3)COO^-\ ½\ Ca^{2+}$ | |
| $C_7F_{15}CF(CF_3)COO^-\ ½\ [H_3N^+C_2H_4NHC_2H_4N^+H_3]$ | |
| $C_8F_{17}CF(CF_3)COO^-\ H_4N+$ | |
| $C_8F_{17}CF(CF_3)COO^-\ K+$ | |
| $C_{10}F_{21}CF(CF_3)COO^-\ H_4N+$ | |
| $C_{10}F_{21}CF(CF_3)COO^-\ K^+$ | |

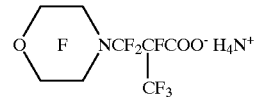

$R_fCF(R'_f)CON(R)(CH_2)_{1-4}COOH$ and sodium salts, where:

$R_f$ is $CF_3(CF_2)_n$ (n=4~9), $R'_f$ is $CF_3(CF_2)_m$ (m=0–1), and

R is $CH_3$ or H 1,1-Dihydroalcohols $C_7F_{15}CF(CF_3)CH_2OH$
$C_7F_{15}CF(C_3F_7)CH_2OH$
$C_{10}F_{21}CF(CF_3)CH_2OH$
$C_6F_{13}CF(CF_3)CH_2OH$
$C_5F_{11}CF(CF_3)CH_2OH$
$C_6F_{13}CF(CF_2CF_3)CH_2OH$
$C_4F_9CF(CF_2CF_3)CH_2OH$ Amides $C_7F_{15}CF(CF_3)CONH_2$
$C_5F_{11}CF(CF_3)CONH(CH_2)_3N(CH_3)_2$
$C_6F_{13}CF(CF_3)CONH(CH_2)_3N(CH_3)_2$
$C_6F_{13}CF(C_2F_5)CONH(CH_2)_3N(CH_3)_2$
$C_7F_{15}CF(CF_3)CONH(CH_2)_3N(CH_3)_2$
$C_7F_{15}CF(C_3F_7)CONH(CH_2)_3N(CH_3)_2$ $C_8F_{17}CF(CF_3)CONH(CH_2)_3N(CH_3)_2$
$C_{10}F_{21}CF(CF_3)CONH(CH_2)_3N(CH_3)_2$

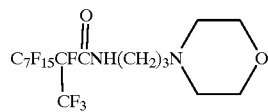

$C_7F_{15}CF(CF_3)CON[C_3H_6N(CH_3)_2]_2$
$CF_3CF_2CF(CF_3)CF(c-C_6F_{11})CONH(CH_2)_3N(CH_3)_2$
$(c-C_6F_{11})_2CFCONH(CH_2)_3N(CH_3)_2$
$C_6F_{13}CF(CF_3)CONH(CH_2)_3CH_3$
$C_7F_{15}CF(CF_3)CONH(CH_2)_3CH_3$
$C_7F_{15}CF(CF_3)CONHCH_2CH_3$
$C_8F_{17}CF(CF_3)CONHCH_2CH_3$
$C_{10}F_{21}CF(CF_3)CONHCH_2CH_3$
$C_7F_{15}CF(CF_3)CONH(CH_2)_2N(CH_3)_2$

Esters $C_7F_{15}CF(CF_3)COOCH_3$
$C_7F_{15}CF(CF_2CF_2CF_3)COOCH_3$
$C_6F_{13}CF(CF_3)COOCH_3$
$C_6F_{13}CF(CF_2CF_3)COOCH_3$
$C_5F_{11}CF(CF_3)COOCH_3$
$C_8F_{17}CF(CF_3)COOCH_3$
$C_{10}F_{21}CF(CF_3)COOCH_3$
$CF_3CF_2CF(CF_3)CF(c-C_6F_{11})COOCH_3$
$(c-C_6F_{11})_2CFCOOCH_3$
$C_5F_{11}CF(CF_3)COOCH_2CH_2CH_3$
$C_6F_{13}CF(CF_3)COOCH_2CH_2CH_3$
$C_7F_{15}CF(CF_3)COOCH_2CH_2CH_3$
$C_8F_{17}CF(CF_3)COOCH_2CH_2CH_3$
$C_{10}F_{21}CF(CF_3)COOCH_2CH_2CH_3$
$C_6F_{13}CF(CF_2CF_3)COOCH_2CH_2CH_3$
$C_7F_{15}CF(CF_3)COOC_6H_5$
$C_7F_{15}CF(CF_3)COOC_6H_4\text{-p-}OCH_3$
$C_7F_{15}CF(CF_3)COOC_6H_4\text{-p-}NO_2$
$C_7F_{15}CF(CF_3)COOCH_2CH_2CH_2N(CH_3)_2$
$C_7F_{15}CF(CF_3)COOCH(CH_3)CH_2N(CH_3)_2$
$C_8F_{17}CF(CF_3)COOCH(CH_3)CH_2N(CH_3)_2$
$C_6F_{13}CF(CF_2CF_3)COOCH_2CH_2NHCO\text{-4-Py}$
$C_7F_{15}CF(CF_3)COOCH_2CH_2NHCO\text{-4-Py}$
$C_6F_{13}CF(CF_3)COOCH_2CH_2NHCO\text{-4-Py}$
$C_8F_{17}CF(CF_3)COOCH_2CH_2NHCO\text{-4-Py}$
$C_8F_{17}CF(CF_3)COOCH_2CH_2\text{-2-Py}$
$C_7F_{15}CF(CF_3)COOCH_2CH_2\text{-2-Py}$
$C_6F_{13}CF(CF_3)COOCH_2CH_2\text{-2-Py}$
$C_5F_{11}CF(CF_3)COOCH_2CH_2\text{-2-Py}$
$C_7F_{15}CF(CF_3)COOCH_2CH_2CH_2N_3$
$C_7F_{15}CF(CF_3)COOCH(CH_2N_3)CH_2OCH_3$
$C_7F_{15}CF(CF_3)COOCH(CH_2N_3)CH_2OCH_2N_3$
(where Py=pyridyl)

Thioesters $C_7F_{15}CF(CF_3)COSCH_2CH_2CH_2CH_3$
$C_8F_{17}CF(CF_3)COSCH_2CH_2CH_2CH_3$
$C_6F_{13}CF(CF_3)COSCH_2CH_2CH_2CH_3$
$C_5F_{11}CF(CF_3)COSCH_2CH_2CH_2CH_3$
$C_7F_{15}CF(CF_3)COSCH_2CH_2COOCH_3$
$C_7F_{15}CF(CF_3)COSCH_2CH_2COOH$
$C_7F_{15}CF(CF_3)COSCH_2CH_2N(CH_3)_2$ Amine Oxide Surfactants $C_5F_{11}CF(CF_3)CONH(CH_2)_3N^+(CH_3)_2O^-$
$C_6F_{13}CF(CF_3)CONH(CH_2)_3N^+(CH_3)_2O^-$
$C_6F_{13}CF(C_2F_5)CONH(CH_2)_3N^+(CH_3)_2O^-$
$C_7F_{15}CF(CF_3)CONH(CH_2)_3N^+(CH_3)_2O^-$
$C_7F_{15}CF(CF_3)CON(C_2H_4OH)(CH_2)_3N^+(CH_3)_2O^-$
$C_7F_{15}CF(C_3F_7)CONH(CH_2)_3N^+(CH_3)_2O^-$
$C_8F_{17}CF(CF_3)CONH(CH_2)_3N^+(CH_3)_2O^-$
$C_{10}F_{21}CF(CF_3)CONH(CH_2)_3N^+(CH_3)_2O^-$
$C_7F_{15}CF(CF_3)CON[(CH_2)_3N^+(CH_3)_2O^-]_2$

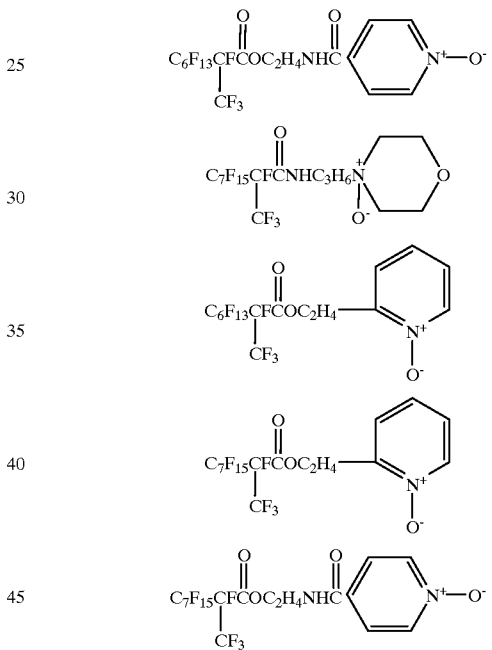

Cationic Surfactants

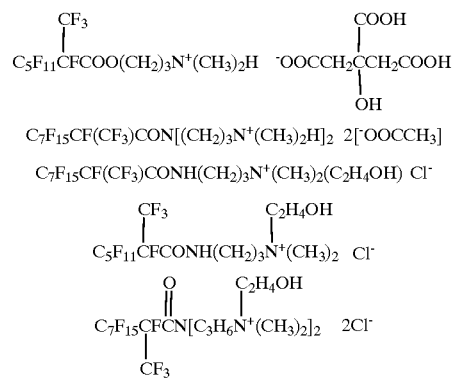

-continued

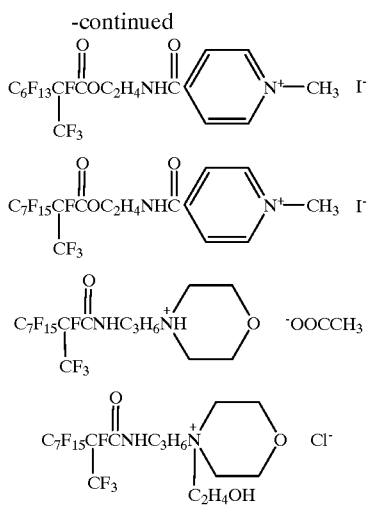

Nonionic Surfactants $C_7F_{15}CF(CF_3)CO(OCH_2CH_2)_{14}OH$
$C_7F_{15}CF(CF_3)CO(OCH_2CH_2)_6OCH_3$
$C_8F_{17}CF(CF_3)CO(OCH_2CH_2)_{16}OCH_3$ Amphoteric Surfactants $C_7F_{15}CF(CF_3)CONH(CH_2)_3N^+(CH_3)_2(C_2H_4COO^-)$
$C_6F_{13}CF(CF_3)CON(C_3H_6SO_3^-)(CH_2)_3N^+(CH_3)_2H$
$C_6F_{13}CF(CF_3)CONH(CH_2)_3N^+(CH_3)_2C_3H_6SO_3^-$

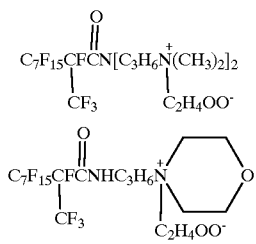

Ethylenically Unsaturated Monomers $C_4F_9CF(CF_2CF_3)COOCH_2CH_2OCOC(CH_3)=CH_2$
$C_5F_{11}CF(CF_3)COOCH_2CH_2OCOCH=CH_2$
$C_5F_{11}CF(CF_3)COOCH_2CH_2OCOC(CH_3)=CH_2$
$C_6F_{13}CF(CF_3)COOCH_2CH_2OCOCH=CH_2$
$C_6F_{13}CF(CF_3)COOCH_2CH_2OCOC(CH_3)=CH_2$
$C_7F_{15}CF(CF_3)COOCH_2CH_2OCOC(CH_3)=CH_2$
$C_7F_{15}CF(CF_3)COOCH_2CH_2OCOCH=CH_2$
$C_8F_{17}CF(CF_3)COOCH_2CH_2OCOCH=CH_2$
$C_8F_{17}CF(CF_3)COOCH_2CH_2OCOC(CH_3)=CH_2$
$C_{10}F_{21}CF(CF_3)COOCH_2CH_2OCOCH=CH_2$
$C_{10}F_{21}CF(CF_3)COOCH_2CH_2OCOC(CH_3)=CH_2$
$C_5F_{11}CF(CF_3)CH_2OCOCH=CH_2$
$C_7F_{15}CF(CF_3)CH_2OCOCH=CH_2$
$C_8F_{17}CF(CF_3)CH_2OCOCH=CH_2$
$C_7F_{15}CF(C_3F_7)CH_2OCOC(CH_3)=CH_2$
$C_{10}F_{21}CF(CF_3)CH_2OCOCH=CH_2$
$C_6F_{13}CF(CF_3)CH_2OCH=CH_2$
$C_5F_{11}CF(CF_3)CH_2OCH_2C_6H_4CH=CH_2$
$C_6F_{13}CF(CF_2CF_3)CH_2OCOC(CH_3)=CH_2$
$C_4F_9CF(CF_2CF_3)CH_2OCH=CH_2$ The α-branched fluoroaliphatic surfactants made in accordance with this invention may be used for any application requiring a surface active agent, including uses as protective coatings and similar applications. Those surfactants detailed herein find particular utility in the formulation of aqueous film-forming foam (AFFF) concentrates such as those used to extinguish hydrocarbon and other flammable liquid fires. Concentrated aqueous fluoroaliphatic surfactant-containing solutions (commonly referred to as "concentrates") that produce an aqueous film-forming foam upon dilution to premix solutions (typically called "premixes") and aeration, must possess a combination of critical properties to be effective in extinguishing flammable liquid fires. These concentrates typically are designated as 1%, 3%, or 6% concentrates and are diluted with 99%, 97%, or 94% fresh or sea water respectively to form the premix. Upon dilution, the premix must exhibit superior foaming characteristics to produce a thick foam blanket that achieves rapid knock down, control, extinguishment, and resistance to reignition of the fire and persists for a significant time after the fire's extinguishment. Aqueous solutions comprising the fluorochemical surfactants detailed supra are useful as concentrates for producing a film-forming foam. Because of the remarkably low surface tensions achieved by these α-branched fluoroaliphatic surfactants, the surface tension of these aqueous solutions is depressed well below the surface tension of a flammable liquid so that a vapor-sealing film draining from their foam readily spreads over the flammable liquid. As a consequence, films produced by these solutions have a strong tendency to reform if disturbed or broken thereby reducing the tendency of a fire to reignite where the film has been disturbed, for example, by wind blowing over the surface of the foam.

In practice of the aqueous film-forming foam concentrates, water delivered through a fire hose under pressure educts typically three percent by volume of a 3% concentrate into the hose line by venturi effect to form a premixture (or "premix") of the concentrate diluted with water. The premix becomes aerated to produce a foam by use of an air-aspirating nozzle located at the outlet end of the hose. The foam is applied to a body of burning fuel or other flammable liquid and spreads quickly as a thick but mobile blanket on the surface for rapid extinguishment. As the foam on the surface of the flammable liquid drains, an aqueous film is formed which, if disturbed or broken, tends to reform to seal hot vapors and prevents reignition of the fire. The concentrates of the invention are considered highly storage stable, passing the U.S. Government specification (MIL-F-24385F) requiring that foaming and film-forming properties of concentrates not be adversely affected if the concentrate and its fresh and sea water premixes (i.e., the concentrate diluted with water) are stored at 65° C. for 10 days, designed to simulate a room temperature storage period of approximately 10 years.

The aqueous film-forming foamable solutions (i.e., concentrates) of the invention comprise an aqueous solution of one or more a-branched fluoroaliphatic surfactants of this invention and one or more water-soluble substantially fluorine-free surfactants. While any of the a-branched fluoroaliphatic surfactants described herein may be employed in the AFFF concentrates of the invention, amphoteric α-branched fluoroaliphatic surfactants are preferred, the amphoteric amine oxide surfactants being particularly preferred. One or more additional fluoroaliphatic amphoteric and/or anionic surfactants, such as a fluorinated aminocarboxylate or a perfluoroalkane sulfonate, may also be added to the formulation. Such additional surfactants are described in U.S. Pat. No. 5,085,786 (Alm et al.), whose description is also incorporated herein by reference.

Usefull fluorine-free surfactants include (1) nonionic surfactants that have a hydrophilic-lipophilic balance (HLB) value of greater than or equal to about 10, (2) anionic surfactants having a carbon chain length containing inclusively from about 6 to about 16 carbon atoms and (3) amphoteric surfactants, used either individually or as blends.

Representative nonionic fluorine-free surfactants include ethylene oxide-based nonionic surfactants such as $C_nH_{2n+1}O(C_2H_4O)_mH$ where n is an integer between about 8 and 18 and m is greater than or equal to about 10; ethoxylated alkylphenols such as

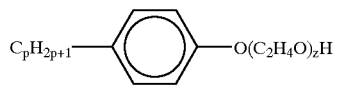

where p is an integer between about 4 and about 12 and z is greater than or equal to about 10, and block copolymers of ethylene oxide and propylene oxide such as Pluronic™ F-77 surfactant (containing at least about 30 wt. % ethylene oxide) available from BASF Corp., Wyandotte, Mich.

Representative short chain anionic fluorine-free surfactants include alkyl sulfates, such as sodium octyl sulfate (e.g., Sipex™ OLS, commerically available from Rhone-Poulenc Corp., Cranberry, N.J.) and sodium decyl sulfate (e.g., Polystep™ B-25, commercially available from Stepan Co., Northfield, Ill.; alkyl ether sulfates such as $C_nH_{2n+1}(OC_2H_4)_2OSO_3Na$, where $6 \leq n \leq 10$ (e.g., Witcolate™ 7093, commerically available from Witco Corp., Chicago, Ill.); and alkyl sulfonates such as $C_nH_{2n+1}SO_3Na$, where $6 \leq n \leq 10$.

Representative amphoteric surfactants include amine oxides, aminopropionates, sultaines, alkyl betaines, alkylamidobetaines, dihydroxyethyl glycinates, imadazoline acetates, imidazoline propionates, and imidazoline sulfonates. Preferred amphoteric surfactants include: salts of n-octyl amine di-propionic acid, e.g., $C_8H_{17}N(CH_2CH_2COOM)_2$ where M is sodium or potassium; Mirataine™ H2C-HA (sodium laurimino dipropionate), Miranol™ C2M-SF Conc. (sodium cocoampho propionate), Mirataine™ CB (cocamidopropyl betaine), Mirataine™ CBS (cocamidopropyl hydroxysultaine), and Miranol™ JS Conc. (sodium caprylampho hydroxypropyl sultaine), all commerically available from Rhone-Poulenc Corp.; and those imidazole-based surfactants described in U.S. Pat. No. 3,957,657 (Chiesa, Jr.), whose description is hereby incorporated by reference.

The abovementioned preferred amphoteric surfactants are especially useful in combination with the fluorinated α-branched fluoroalkylcarbonyl amidoamine oxide surfactants of this invention to formulate superior AFFF agents. Not only is the foamability of the agents excellent, but the surface tensions of the premixes made from the concentrates are very low, for example, below about 17 dynes/cm, and the interfacial tension at about 2.5 dynes/cm is optimal for film formation. This allows the premixes to form thick and stable non-emulsified aqueous films which spread over the fuel or other flammable liquid, leading to excellent fire-fighting performance.

Additional components may optionally be added to the AFFF concentrates such as water soluble solvents used to facilitate solubilization of the fluoroaliphatic surfactant or surfactants, including ethylene glycol, glycerol, butyl Carbitol™, dipropylene glycol mono-n-propyl ether, dipropylene glycol monomethyl ether, and hexylene glycol. These solvents may also act as foam stabilizers and freeze-protection agents. Additional components, such as stabilizers and thickeners, can be incorporated into the concentrates of the invention to enhance the foam stability property of the foam produced after aeration of the premix. Examples of stabilizers and thickeners include partially hydrolyzed protein, starches, polyvinyl resins (e.g., polyvinyl alcohol, polyvinyl pyrolidone, polyacrylamides, carboxyvinyl polymers), alkanolamide surfactants, long chain alkanols, poly(oxyethylene)-glycol, guar gum and locust bean gum. In particular, polysaccharide resins, such as xanthan gum and other biogums, can be incorporated as foam stabilizers in concentrates intended to be used on polar solvent fires such as alcohols, ketones, and ethers. Other useful resins for improving polar solvent resistance are fluorochemically modified acrylates or polymers. Corrosion inhibitors, buffers, antimicrobial or other preservative agents, and divalent ion salts may also be employed. Additional components that may be added to the AFFF formulations of the invention are detailed in U.S. Pat. Nos. 5,085,786 (Alm et al.) and 3,772,195 (Francen), both of whose descriptions are incorporated herein by reference for such purpose.

Typically, between 1 and 10 percent by weight of the fluorochemical surfactant or surfactants and between 1 and 30 percent by weight of the fluorine-free surfactant or surfactants will be employed to make the AFFF concentrate. The total amount of solids attributable to other additive components, if such components are present, should be such that the premix maintains its foamability and such that the density of the foam prepared therefrom is less than about 1 g/cc. Generally, the amount of solids in the concentrate attributable to said optional components will be less than about 50 weight percent, preferably less than about 30 weight percent, of the concentrate. The amount of solvent used in the concentrate typically is between 5 and 40 percent by weight of the concentrate. Generally, the amount of solids (i.e. nonvolatiles) attributable to non-surfactant and non-solvent components such as stabilizers, thickeners, corrosion inhibitors, buffers, antimicrobial agents, and divalent ion salts will be less than about 20 percent by weight, preferably less than about 10 weight percent of the concentrate.

The following examples are offered to aid in a better understanding of the present invention. These examples are not to be construed as an exhaustive compilation of all embodiments of the present invention and are not to be unnecessarily construed as limiting the scope of this invention.

EXAMPLES

Test Methods

The following test methods and procedures were used to evaluate the performance of the fluorinated emulsifiers, surfactants and AFFF agents made therefrom:

Surface Tension (ST): Surface tensions of aqueous surfactant solutions and 3% AFFF premixes were measured in units of dynes/cm using a K-12 Processor Tensiometer and 665 Dosimat™ measuring method with Software K 122, available from Krüss GmbH, Hamburg Germany. The surface tension should be as low as possible for the premix to have its maximum film-forming effectiveness.

Interfacial Tension (IT): Interfacial tensions (in dynes/cm) of the interface formed between 3% premixes and n-heptane (>99% purity, surface tension=20.4 dynes/cm) were measured using a K-12 Processor Tensiometer. The interfacial tension should be as high as possible to produce thick, stable films and to avoid emulsification of the fuel, yet should be sufficiently low to allow for a positive spreading coefficient.

Spreading Coefficient (SC): The Spreading Coefficient (in dynes/cm), is calculated from the surface and interfacial tension values measured with the premixes as follows:

$$SC=ST_{(fuel)}-[ST_{(premix)}+IT_{(premix/fuel)}]$$

A positive Spreading Coefficient is a minimum requirement for the premix to form a vapor sealing aqueous film on the surface of the fuel.

Critical Micelle Concentration (CMC): The critical micelle concentration is defined as the concentration at which further surface tension is no longer lowered with increasing levels of surfactant. To determine CMC, surface tension is measured as a function of surfactant concentration using a K-12 Processor Tensiometer in conjunction with a 665 Dosimat automatic surfactant injection device (also commercially available from Krüss GmbH). Surface tension is then plotted vs. log concentration and the data points are connected. The resulting curve has a nearly horizontal flat portion at concentrations above the CMC and has a negative steep slope at concentrations below the CMC. The CMC is defined as the lowest surfactant concentration in the horizontal flat portion of the curve.

Foam Expansion and Drain Time: Foam expansion, defined as the volume of foam produced divided by the volume of liquid used to produce the foam, is determined as described in U.S. Government Military Specification MIL-F-24335, Revision F. In this test, a standard National Foam System 2 gal/min (7.6 L/min) nozzle is used to generate foam from a 3% premix (i.e., 3 parts by volume of concentrate mixed with 97 parts by volume of fresh or sea water) contained in a stainless steel pressurized tank. The foam is deflected off a 45° backstop into a 1-L tared graduated cylinder, and the weight of the cylinder plus foam is recorded in grams. The foam expansion is calculated by dividing the actual volume (mL) (i.e., not the nominal 1-L volume) of the graduate by the weight (g) of the foam.

The 25% drain time for the foam, also described in U.S. Government Military Specification MIL-F-24385, Revision F, is defined as the amount of time after foam collection for 25% of the weight (i.e., volume) of foam to drain to the bottom of the graduate (read as milliliters in the graduated cylinder, assuming a specific gravity of 1.0).

Film-Forming and Sealing: The Film-Forming and Sealing Test determines whether an AFFF premix is capable of forming a stable film on n-heptane. In this test, an inverted No. 8 flathead screw is placed in the center of a 10 cm diameter glass petri dish containing 40 mL of n-heptane (>99% purity, surface tension=20.4 dynes/cm). An aqueous film is generated on the n-heptane surface by gently applying dropwise 0.75 mL of test premix solution from a 1 mL disposable syringe to the tip of the inverted screw over an approximately 30 to 60 second time period. Two minutes after applying the first drop of premix solution, a small flame is moved approximately 0.5 inch (1.3 cm) over the n-heptane surface for about 10 seconds. For a good vapor seal, no sustained ignition shall result, though a small intermittent flash is permitted.

Fire Extinguishment and Burnback Test: The fire test procedure used to evaluate AFFF agents in the examples is outlined in the U.S. Department of Defense Military Specification No. MIL-F-24385, Revision F, Section 4.7.13.2. According to this procedure, 3.0 gallons of a 3.0% (vol) premix is made by mixing 3 volumes of a 3% concentrate with 97 volumes of synthetic sea water (the sea water being made in accordance with ASTM D1141). The premix is poured into a tank with attached hose and foam nozzle, and the filled tank is pressurized. Then 15 gallons (57 L) of automotive gasoline is poured onto a water base contained in a 50 ft$^2$ (4.7 m$^2$) circular pit. After the gasoline is ignited and allowed to preburn for 10 seconds, an operator aggressively attacks the fire using foam generated from the premix by passing the premix through a National Foam System air-aspirating nozzle at a flow rate of 2.0 gal/min. The percent extinguishment of the fire is recorded at every 10 second mark until the fire is fully extinguished. Also, the exact extinguishment time is recorded. The efficiency of fire extinguishment is quantified as the "40 second summation," which is defined as the sum of the percent extinguishment values recorded at the 10, 20, 30 and 40 second marks. After extinguishment, the foam is continually applied to the pit until the 90 second mark, at which time the premix solution is exhausted.

Within 60 seconds after extinguishment, a one foot diameter circular pan containing burning gasoline is placed at the center of the circular pit. The time for 25% (12.5 ft$^2$, or 1.16 m$^2$) of the foam-covered area to become reinvolved in flames is measured and is recorded as the "25% burnback time."

EXAMPLES

A. Synthesis of α-Branched Fluoroalkylcarbonyl Fluorides

Example A1

$C_7F_{15}CF(CF_3)COF$, an α-branched perfluoroalkylcarbonyl fluoride, was prepared using the following electrochemical fluorination procedure.

Using an electrochemical fluorination cell of the type described in U.S. Pat. No. 2,713,593 (Brice et al.), a mixture of 94% (wt) $C_7H_{15}CH(CH_3)COCl$ (275.4 g) and 6% (wt) dimethyldisulfide (DMDS) (17.6 g) was electrochemically fluorinated in boiling HF at 1380 torr and 38° C. contained in a 750 mL cell equipped with a 0.037 m$^2$ nickel anode for a total time of 300 hours using an average current of 7.74 amps and average conductivity of 6.8 volts during the electrofluorination. The production rate of crude perfluorinated carbonyl fluoride increased throughout the run to a peak level of 20.0 g/50 amp-hours. Yield of functional perfluoroalkylcarbonyl fluorides produced was about 17% of theoretical based on cell crude, according to a GC/FTIR analysis of an aliquot derivatized into the methyl ester. Subsequent analysis of the functional perfluoroalkylcarbonyl fluoride mixture using GC/MS showed 21% to be $C_7F_{15}CF(CF_3)COF$.

The following a-branched perfluoroalkylcarbonyl fluorides (Examples A2–A3) were synthesized from their unfluorinated carbonyl chloride analogues using the essentially the same electrochemical fluorination procedure as described in Example A1.

| Ex. | |
|---|---|
| A2. | $C_6F_{13}CF(CF_3)COF$ |
| A3. | $C_4F_9CF(CF_2CF_3)COF$ |

Synthesis of Methyl Ester Intermediates By Direct Fluorination $C_6F_{13}CF(CF_3)COOCF_3$ was prepared from $C_6H_{13}CH(CH_3)COOCH_3$ using the following direct fluorination procedure. A direct fluorination run was made using a reactor system similar to the one described in U.S. Pat. No. 5,488,142. 6449 g of 3M Brand PF-5052 Performance Fluid was charged to the gas-liquid separator of the reactor system and, using a circulating pump, was circulated through the reactor system at a rate of 11.8 kg/min. Nitrogen was introduced into the circulating stream of PF-5052 at a rate of 2007 cm$^3$/min, and the temperature of the circulating stream was maintained at 28° C., maintaining the temperatures of the two overhead condensers at 10° C. and −32° C. respectively. After sufficient nitrogen had purged the vapor space to drop the oxygen concentration to below 0.1% (as measured in the gas stream exiting the system), fluorine was introduced into the tubular reactor at 538 cm$^3$/min. A feed of 464 g of $C_6H_{13}CH(CH_3)COOCH_3$ was gradually introduced into the PF-5052 in the mixing zone to react with the fluorine over a period of 59 hours. After all of the organic feed had been added, the diluted fluorine addition was continued until the oxygen gas content of the gaseous effluent of alumina columns used as scrubbers rose to greater than 5% (i.e., the alumina reacts with fluorine and releases oxygen). The fluorine supply was shut off and the nitrogen supply was continued until unreacted fluorine was purged from the system, after which the circulating pump was shut off. Percent yield of $C_6F_{13}CF(CF_3)COOCF_3$ was 72%. The product was purified by distillation.

The following fluorinated ester derivatives were prepared from their hydrocarbon analogues using an analogous direct fluorination procedure to that described immediately above.

| Ex. | | Percent Yield |
| --- | --- | --- |
| | $C_5F_{11}CF(CF_3)COOCF_3$ | 86 |
| | $C_7F_{15}CF(CF_3)COOCF_3$ | 85 |
| | $C_8F_{17}CF(CF_3)COOCF_3$ | 91 |
| | $C_{10}F_{21}CF(CF_3)COOCF_3$ | 76 |
| | $C_{16}F_{33}CF(CF_3)COOCF_3$ | Not Recorded (N/R) |
| | $C_6F_{13}CF(C_2F_5)COOCF_3$ | 72 |
| | $C_6F_{13}CF(C_3F_7)COOCF_3$ | N/R |
| | $C_7F_{15}CF(C_3F_7)COOCF_3$ | 82 |
| | $C_6F_{13}CF(C_4F_9)COOCF_3$ | N/R |

Example A4

In Example A4, $C_7F_{15}CF(CF_3)COF$ was prepared from $C_7F_{15}CF(CF_3)COOCF_3$. To 4500 g (7.73 mol) of $C_7F_{15}CF(CF_3)COOCF_3$ in 1700 mL of acetone was added 200 g (1.2 mol) of KI in one portion at room temperature. The mixture was stirred for 2 hours at room temperature and then for another 2 hours at 40° C. The inorganic salt by-product was filtered off, and the bottom layer, containing the desired product, was recovered by distillation at 142–147° C. (3598 g, 90.2% yield). The structure of the desired product, $C_7F_{15}CF(CF_3)COF$, was confirmed by analysis of IR and $^{19}F$ NMR spectra.

(By word of Caution to the reader: Running this size reaction generates significant concentrations of hazardous carbonyl fluoride ($COF_2$), and care must be taken to remove the $COF_2$ by suitable absorption in aqueous alkali.)

Examples A5-A13

The following fluoroalkylcarbonyl fluorides were prepared from their perfluorinated methyl ester analogues using the same KI reaction procedure as described in Example A4.

| Ex. | | Percent Yield |
| --- | --- | --- |
| A5. | $C_5F_{11}CF(CF_3)COF$ | 79 |
| A6. | $C_6F_{13}CF(CF_3)COF$ | 84 |
| A7. | $C_8F_{17}CF(CF_3)COF$ | 92 |
| A8. | $C_{10}F_{21}CF(CF_3)COF$ | 88 |
| A9. | $C_{16}F_{33}CF(CF_3)COF$ | N/R |
| A10. | $C_6F_{13}CF(C_2F_5)COF$ | 84 |
| A11. | $C_6F_{13}CF(C_3F_7)COF$ | N/R |
| A12. | $C_7F_{15}CF(C_3F_7)COF$ | 85 |
| A13. | $C_6F_{13}CF(C_4F_9)COF$ | N/R |

B. Synthesis of a-Branched Perfluoroalkylcarboxamides

Example B1

$C_7F_{15}CF(CF_3)CONH(CH_2)_3N(CH_3)_2$ was prepared by reacting $C_7F_{15}CF(CF_3)COF$ (from Example A1) with N,N-dimethylaminopropylamine using the following procedure. 1084 g (2.1 mol) of $C_7F_{15}CF(CF_3)COF$ was added dropwise to a mixture of 320 g (3.1 mol) of N,N-dimethylaminopropylamine and 1200 mL of tetrahydrofuran (THF) at room temperature over a period of approximately 2 hours. After addition was completed, the mixture was refluxed for 3 hours. After being allowed to cool, the THF solution was washed twice with an aqueous solution of $NaHCO_3$, then was washed twice with deionized water. The aqueous portion was extracted twice with 150 mL aliquots of chloroform, the chloroform solutions were combined with the THF solution, and the resulting combined solution was dried over anhydrous $MgSO_4$. Solvent was removed under reduced pressure and the residue was distilled under reduced pressure to give 1025 g (82% yield) of the desired product, whose structure was confirmed by IR spectra and by $^1H$, $^{13}C$ and $^{19}F$ NMR spectra.

The following a-branched perfluoroalkylcarbonamidoamine and perfluoroalkylcarbonamide intermediates (Examples B2–B 15) were synthesized by reacting their α-branched perfluoroalkylcarbonyl fluoride analogues shown in Examples A1–A13 with N,N-dimethylaminopropylamine, dimethylaminopropanol or primary mono- or diamines using the same reaction procedure as described in Example B1, keeping the molar ratio of carbonyl fluoride to active hydrogen-containing amine the same. In some examples, diisopropyl ether (IPE) was used as the solvent instead of THF.

| Ex. | | Amine Used |
| --- | --- | --- |
| B2. | $C_5F_{11}CF(CF_3)CONH(CH_2)_3N(CH_3)_2$ | $H_2N(CH_2)_3N(CH_3)_2$ |
| B3. | $C_6F_{13}CF(CF_3)CONH(CH_2)_3N(CH_3)_2$ | $H_2N(CH_2)_3N(CH_3)_2$ |
| B4. | $C_8F_{17}CF(CF_3)CONH(CH_2)_3N(CH_3)_2$ | $H_2N(CH_2)_3N(CH_3)_2$ |
| B5. | $C_{10}F_{21}CF(CF_3)CONH(CH_2)_3N(CH_3)_2$ | $H_2N(CH_2)_3N(CH_3)_2$ |
| B6. | $C_6F_{13}CF(CF_2CF_3)CONH(CH_2)_3N(CH_3)_2$ | $H_2N(CH_2)_3N(CH_3)_2$ |
| B7. | $C_7F_{15}CF(CF_2CF_2CF_3)CONH(CH_2)_3N(CH_3)_2$ | $H_2N(CH_2)_3N(CH_3)_2$ |
| B8. | $C_6F_{13}CF(CF_3)CONH(CH_2)_3CH_3$ | $H_2N(CH_2)_3CH_3$ |
| B9. | $C_7F_{15}CF(CF_3)CONH(CH_2)_3CH_3$ | $H_2N(CH_2)_3CH_3$ |
| B10. | $C_7F_{15}CF(CF_3)CONH(CH_2)_2N(CH_3)_2$ | $H_2N(CH_2)_2N(CH_3)_2$ |
| B11. | $C_7F_{15}CF(CF_3)CONHCH_2CH_3$ | $H_2NCH_2CH_3$ |
| B12. | $C_8F_{17}CF(CF_3)CONHCH_2CH_3$ | $H_2NCH_2CH_3$ |
| B13. | $C_{10}F_{21}CF(CF_3)CONHCH_2CH_3$ | $H_2NCH_2CH_3$ |

-continued

| Ex. | Amine Used |
|---|---|
| B14. | $C_7F_{15}\overset{\underset{\mid}{CF_3}}{\underset{\mid}{C}}FCNH(CH_2)_3N\!\!\begin{pmatrix}O\end{pmatrix}$    $H_2N(CH_2)_3N\!\!\begin{pmatrix}O\end{pmatrix}$ |

Example B15

$C_7F_{15}CF(CF_3)CON[(C_3H_6N(CH_3)_2]_2$ was prepared by reacting $C_7F_{15}CF(CF_3)COF$ (from Example A1) with $HN[(C_3H6N(CH_3)_2]_2$ using the following procedure. 25.8 g (0.05 mol) of $C_7F_{15}CF(CF_3)COF$ was added to a mixture of 18.7 g (0.10 mole) of $HN[(C_3H_6N(CH_3)_2]_2$ and 50.5 g of diisopropyl ether in a 3-necked round bottom flask equipped with stirrer, heater, thermometer and reflux condensor, and the resulting mixture was refluxed for 3 hours and was allowed to cool. Then 150 g of deionized water was added and the contents of the flask were stirred vigorously. The pH of the contents was adjusted downward from 10 to 9 using acetic acid, resulting in the formation of two distinct phases. The lower aqueous phase was drained, saving the upper organic phase. The organic phase was then washed with 50 g of water (readjusting the pH of the contents to 9), and the water phase was again drained. The washed organic phase was dried over anhydrous $MgSO_4$, was filtered, and was evaporated to dryness in a vacuum oven, resulting in 30.0 g of an amber oil which was the desired product (as confirmed by IR and $^1H$ NMR analysis).

C. Synthesis of α-Branched Perfluorocarboxylic Acid Methyl Esters

Example C1

The methyl ester, $C_7F_{15}CF(CF_3)COOCH_3$, was prepared using the following procedure. $C_7F_{15}CF(CF_3)COOCF_3$ was mixed with a stoichiometric excess of methanol, and the mixture was refluxed with stirring for 2 hours. The unreacted methanol was distilled off and the desired methyl ester, $C_7F_{15}CF(CF_3)COOCH_3$, was washed with deionized water, was dried over anhydrous $MgSO_4$, and was purified by distillation.

The following methyl esters ( Examples C2–C9) were synthesized using the same procedure as described in Example C1.

| Ex. | |
|---|---|
| C2. | $C_7F_{15}CF(CF_2CF_2CF_3)COOCH_3$ |
| C3. | $C_6F_{13}CF(CF_3)COOCH_3$ |
| C4. | $C_6F_{13}CF(CF_2CF_3)COOCH_3$ |
| C5. | $C_5F_{11}CF(CF_3)COOCH_3$ |
| C6. | $C_8F_{17}CF(CF_3)COOCH_3$ |
| C7. | $C_{10}F_{21}CF(CF_3)COOCH_3$ |
| C8. | $CF_3CF_2CF(CF_3)CF(c-C_6F_{11})COOCH_3$* |
| C9. | $(c-C_6F_{11})_2CFCOOCH_3$* |

*The cyclic perfluorinated methyl ester precursors to these methyl esters were made according to the procedure described in Example A4

D. Synthesis of α-Branched Perfluorocarboxylic Acid (Meth)acrylates and Longer Chain Esters

Example D1

The acrylate, $C_7F_{15}CF(CF_3)COOCH_2CH_2OCOCH=CH_2$, was prepared using the following procedure. 155 g (0.3 mol) $C_7F_{15}CF(CF_3)COF$ (from Example A1) was added dropwise at room temperature to a mixture of 41 g (0.35 mol) of 2-hydroxyethylacrylate, 31 g (0.3 mol) of triethylamine, and 350 mL of THF. After addition was complete, the resulting mixture was allowed to react by heating to 50° C. with stirring for 3 hours. The reaction mixture was washed 3 times with deionized water, the resulting aqueous solutions were poured together and extracted with chloroform, the resulting chloroform solution was combined with the reaction mixture, and reaction mixture/chloroform combination was dried over anhydrous $MgSO_4$. The solvent was then removed and the residue was distilled at 95–102° C. and 3 mm Hg to yield 130 g of desired product, whose structure was confirmed using IR and NMR analysis.

The following acrylates, methacrylates and alkyl-, aryl-, substituted alkyl- and substituted aryl esters (Examples D2–D3 1) were synthesized using the same procedure as described in Example D1.

| Ex. | |
|---|---|
| D2. | $C_8F_{17}CF(CF_3)COOCH_2CH_2OCOCH=CH_2$ |
| D3. | $C_7F_{15}CF(CF_3)COOCH_2CH_2OCOC(CH_3)=CH_2$ |
| D4. | $C_8F_{17}CF(CF_3)COOCH_2CH_2OCOC(CH_3)=CH_2$ |
| D5. | $C_6F_{13}CF(CF_3)COOCH_2CH_2OCOCH=CH_2$ |
| D6. | $C_6F_{13}CF(CF_3)COOCH_2CH_2OCOC(CH_3)=CH_2$ |
| D7. | $C_5F_{11}CF(CF_3)COOCH_2CH_2OCOCH=CH_2$ |
| D8. | $C_5F_{11}CF(CF_3)COOCH_2CH_2OCOC(CH_3)=CH_2$ |
| D9. | $C_{10}F_{21}CF(CF_3)COOCH_2CH_2OCOCH=CH_2$ |
| D10. | $C_{10}F_{21}CF(CF_3)COOCH_2CH_2OCOC(CH_3)=CH_2$ |
| D11. | $C_4F_9CF(CF_2CF_3)COOCH_2CH_2OCOC(CH_3)=CH_2$ |
| D12. | $C_5F_{11}CF(CF_3)COOCH_2CH_2CH_2CH_3$ |
| D13. | $C_6F_{13}CF(CF_3)COOCH_2CH_2CH_2CH_3$ |
| D14. | $C_7F_{15}CF(CF_3)COOCH_2CH_2CH_2CH_3$ |
| D15. | $C_8F_{17}CF(CF_3)COOCH_2CH_2CH_2CH_3$ |
| D16. | $C_{10}F_{21}CF(CF_3)COOCH_2CH_2CH_2CH_3$ |
| D17. | $C_6F_{13}CF(CF_2CF_3)COOCH_2CH_2CH_2CH_3$ |
| D18. | $C_7F_{15}CF(CF_3)COOC_6H_5$ |
| D19. | $C_7F_{15}CF(CF_3)COOC_6H_4\text{-p-}OCH_3$ |
| D20. | $C_7F_{15}CF(CF_3)COOC_6H_5\text{-p-}NO_2$ |
| D21. | $C_6F_{13}CF(CF_2CF_3)COOCH_2CH_2NHCO\text{-4-Py}$ |
| D22. | $C_7F_{15}CF(CF_3)COOCH_2CH_2NHCO\text{-4-Py}$ |
| D23. | $C_6F_{13}CF(CF_3)COOCH_2CH_2NHCO\text{-4-Py}$ |
| D24. | $C_8F_{17}CF(CF_3)COOCH_2CH_2NHCO\text{-4-Py}$ |
| D25. | $C_8F_{17}CF(CF_3)COOCH_2CH_2\text{-2-Py}$ |
| D26. | $C_7F_{15}CF(CF_3)COOCH_2CH_2\text{-2-Py}$ |
| D27. | $C_6F_{13}CF(CF_3)COOCH_2CH_2\text{-2-Py}$ |
| D28. | $C_5F_{11}CF(CF_3)COOCH_2CH_2\text{-2-Py}$ |
| D29. | $C_7F_{15}CF(CF_3)COOCH_2CH_2CH_2N_3$ |
| D30. | $C_7F_{15}CF(CF_3)COOCH(CH_2N_3)CH_2OCH_3$ |
| D31. | $C_7F_{15}CF(CF_3)COOCH(CH_2N_3)CH_2OCH_2N_3$ |
| D32. | $C_7F_{15}CF(CF_3)COOCH(COOCH_3)(CH_3)$ |
| D33. | $C_7F_{15}CF(CF_3)COOCH(CH_3)CH_2N(CH_3)_2$ |
| D34. | $C_8F_{17}CF(CF_3)COOCH(CH_3)CH_2N(CH_3)_2$ |
| D35. | $C_5F_{11}CF(CF_3)COO(CH_2)_3N(CH_3)_2$ |

(where Py = pyridyl)

The acrylate and methacrylate esters from Examples D1–D11 were fully recoverable with essentially no degradation after being stirred with concentrated aqueous ammonium hydroxide for a period of 2 days. Thus, α-branched esters were shown to be hydrolytically stable, even in basic solution, so that they may be polymerized using emulsion polymerization. In contrast, similar esters of a non-α-branched perfluorocarboxylic acid, for example, $C_7F_{15}COOCH_2CH_2OCOCH=CH_2$, were readily hydrolyzed under comparable conditions.

E. Synthesis of α-Branched Perfluoroalkylcarbonyl Amine Oxide Surfactants

Example E1

$C_7F_{15}CF(CF_3)CONH(CH_2)_3N^+(CH_3)_2O^-$ was prepared by reacting $C_7F_{15}CF(CF_3)CONH(CH_2)_3N(CH_3)_2$ (from Example B1) with hydrogen peroxide using the following procedure. 12.0 g (0.02 mol) of $C_7F_{15}CF(CF_3)CONH(CH_2)_3N(CH_3)_2$ and 12.0 g of ethanol were added to a 3-necked round-bottom flask equipped with stirrer, thermometer and water condensor. To this stirred solution was added 5.7 g (0.05 mol) of 30% aqueous $H_2O_2$ over a 5 minute period, and stirring was continued for 72 hours at ambient lab temperature. The resulting solution was refluxed for a 4-hour period, 0.2 g of decolorizing/activated charcoal was added, and the mixture was gently refluxed for an additional 3 hours. The reacted mixture was filtered through Celite™ filter aid and the filtrate was evaporated to dryness at aspirator vacuum at 70° C. for 3 hours to produce a viscous yellow oil. IR analysis and $^1H$ and $^{19}F$ NMR analysis were consistent with the structure $C_7F_{15}CF(CF_3)CONH(CH_2)_3N^+(CH_3)_2O^-$.

The following α-branched tertiary perfluoroalkylcarbonamidoamine oxides (Examples E2–E9) were synthesized by reacting their ax-branched tertiary perfluoroalkylcarbonamidoamine analogues with hydrogen peroxide using the same reaction procedure as that described in Example E1, keeping the molar ratio of reactants the same:

| Ex. | Amine Oxide |
|---|---|
| E2 | $C_5F_{11}CF(CF_3)CONH(CH_2)_3N^+(CH_3)_2O^-$ |
| E3 | $C_6F_{13}CF(CF_3)CONH(CH_2)_3N^+(CH_3)_2O^-$ |
| E4 | $C_8F_{17}CF(CF_3)CONH(CH_2)_3N^+(CH_3)_2O^-$ |
| E5 | $C_{10}F_{21}CF(CF_3)CONH(CH_2)_3N^+(CH_3)_2O^-$ |
| E6 | $C_6F_{13}CF(C_2F_5)CONH(CH_2)_3N^+(CH_3)_2O^-$ |
| E7 | $C_7F_{15}CF(C_3F_7)CONH(CH_2)_3N^+(CH_3)_2O^-$ |
| E8 | $C_7F_{15}CF(CF_3)CON(C_2H_4OH)(CH_2)_3N^+(CH_3)_2O^-$ |
| E9 | ![structure: C_7F_15CFCNHC_3H_6-morpholine N-oxide with CF_3] |

Example E10

The perfluoroalkylcarbonyl pyridinium amine oxide,

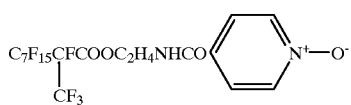

was prepared using the following procedure. A mixture of 0.04 mol of $C_7F_{15}CF(CF_3)COOCH_2CH_2NHCO$-4-Py (from Example D23) and 0.1 mol of peracetic acid in 100 mL of ethanol was allowed to react by refluxing for 9 hours. Then 2 g of activated carbon was added and the mixture was allowed to reflux for 3 additional hours. The mixture was filtered and the solvent was removed from the filtrate to give the desired product.

The following a-branched tertiary perfluoroalkylcarbonyl pyridinium amine oxides (Examples E11–E13) were synthesized by reacting their α-branched perfluoroalkylcarbonyl pyridine analogues with peracetic acid using the same reaction procedure as that described in Example E11, keeping the molar ratio of reactants the same:

| Ex. | Amine Oxide |
|---|---|
| E11 | $C_6F_{13}CFCOC_2H_4NHC$— pyridinium N-oxide, CF_3 |
| E12 | $C_6F_{13}CFCOC_2H_4$— pyridinium N-oxide, CF_3 |
| E13 | $C_7F_{15}CFCOC_2H_4$— pyridinium N-oxide, CF_3 |

Example E14

$C_7F_{15}CF(CF_3)CON[(CH_2)_3N^+(CH_3)_2O^-]_2$ was prepared using the following procedure. To 10.0 g (0.0146 mol) of $C_7F15CF(CF_3)CON[C_3H6N(CH_3)_2]_2$ (from Example B16) was added 10.0 g of ethanol. 7.9 g (0.07 mol) of 30% aqueous $H_2O_2$ was added, and the mixture was heated at 70° C. for 5 hours, then was allowed to cool to room temperature. After cooling, the mixture was refluxed for 1 hour; then 0.2 g of activated carbon was added and the mixture was refluxed for an additional 3 hours. The solution was filtered and the solvent was removed at 70° C. and 25 torr to give 10.7 g of the desired product, a yellow oil.

F. Synthesis of α-Branched Perfluoroalkylcarbonyl Cationic Surfactants

Example F1

The pyridinium salt,

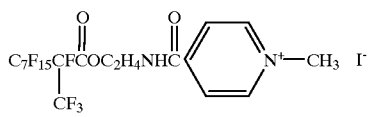

was prepared using the following procedure. $C_7F_{15}CF(CF_3)COOCH_2CH_2NHCO$-4-Py (from Example D22) was added to a slight stoichiometric excess of methyl iodide in THF, and the mixture was allowed to react by refluxing for 2 hours. The resultant orange solid was filtered off, was washed with THF, and was recrystallized from ethanol as yellow crystals.

Example F2

The following a-branched perfluoroalkylcarbonyl pyridinium iodide was synthesized by reacting the analogous α-branched perfluoroalkylcarbonyl pyridine (from Example D23) with methyl iodide using the same reaction procedure as described in Example F1, keeping the molar ratio of reactants the same:

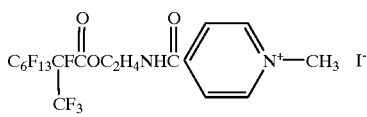

Example F3

10.0 g (0.02 mol) of the amidoamine from Example B2 and 1.77 g (0.022 mol) of 2-chloroethanol were added to a round bottom flask. The mixture was heated and stirred at 70° C. for 24 hours and was cooled to give an amber resinous material. Using infrared spectroscopy, the structure of the product was confirmed to be the desired cationic fluoroaliphatic surfactant,

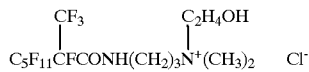

Example F4

The following a-branched perfluoroalkylcarbonyl amidoamines (Example F4–F6) were synthesized using a synthetic procedure analogous to that described in Example F3 except that the amides of Examples B1, B14 and B15 respectively were substituted for that from Example B2.

| Ex. | |
|---|---|
| F4. | 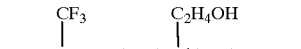 |
| F3 | 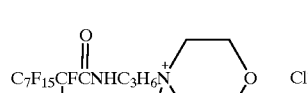 |
| F6 | 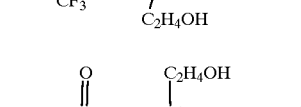 |

Example F7

1.0 g (0.0016 mol) of the amidoamine from Example B14, 1.22 g (0.02 mol) of glacial acetic acid and 1.11 g of deionized water were combined in a round bottom flask and stirred for 1 hour at ambient temperature to form a clear solution of the desired surfactant salt,

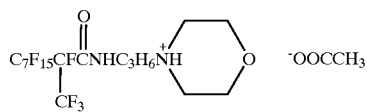

Example F8

10.0 g (0.02 mol) of $C_5F_{11}CF(CF_3)COO(CH_2)_3N(CH_3)_2$ (from Example D35), 3.84 g (0.02 mol) of citric acid (>99.5% pure) and 10.0 g of ethanol were combined in a round bottom flask and stirred while warming until a clear solution was formed. The ethanol was evaporated off under reduced pressure and the resulting product was further dried in a vacuum oven at 70° C. and 25 torr for 4 hours to provide the surfactant citrate salt. Analysis by IR spectroscopy confirmed the structure to be

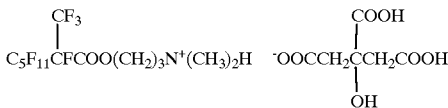

Example F9

The amine salt, $C_7F_{15}CF(CF_3)CON[C_3H_6N^+(CH_3)_2H]_2$ $2[^-OOCCH_3]$, was prepared using the following procedure. 5.0 g of $C_7F_{15}CF(CF_3)CON[C_3H_6N(CH_3)_2]_2$ (from Example B15) was mixed with 5.0 g of glacial acetic acid and 10.0 g of deionized water to form an aqueous solution of the desired amine salt.

G. Synthesis of α-Branched Perfluoroalkylcarbonyl Thioesters

Example G1

The thioester, $C_7F_{15}CF(CF_3)COSCH_2CH_2CH_2CH_3$, was prepared using the following procedure. A mixture consisting of 0.02 mol $C_7F_{15}CF(CF_3)COF$ (from Example A1), 0.025 mol of 1-butanethiol, 0.025 mol of pyridine and 50 mL of THF was allowed to react by refluxing for 3 hours. Dilute aqueous HCl was added with mixing, producing two phases. After separating the organic phase, the aqueous phase was extracted twice with 30 mL of chloroform and the two chloroform solutions were combined with the organic phase. Solvent was then removed from the chloroform/organic phase mixture and the residue was distilled to give the desired product having a boiling range of 202–205° C.

The following thioesters (Examples G2–G7) were synthesized using the same procedure as described in Example G1.

| Ex. | |
|---|---|
| G2. | $C_8F_{17}CF(CF_3)COSCH_2CH_2CH_2CH_3$ |
| G3. | $C_6F_{13}CF(CF_3)COSCH_2CH_2CH_2CH_3$ |
| G4. | $C_5F_{11}CF(CF_3)COSCH_2CH_2CH_2CH_3$ |
| G5. | $C_7F_{15}CF(CF_3)COSCH_2CH_2COOCH_3$ |
| G6. | $C_7F_{15}CF(CF_3)COSCH_2CH_2COOH$ |
| G7. | $C_7F_{15}CF(CF_3)COSCH_2CH_2N(CH_3)_2$ |

H. Synthesis of α-Branched 1,1-Dihydroperfluoroalkanols

Example H1

The dihydroperfluoroalkanol, $C_7F_{15}CF(CF_3)CH_2OH$, was prepared using the following procedure. 4 g of sodium borohydride was added in portions to a mixture of 25 g of $C_7F_{15}CF(CF_3)COF$ (from Example A1) and 100 mL of THF at room temperature. The resulting mixture was stirred overnight at room temperature. Deionized water was then added carefully to destroy the excess sodium borohydride and hydrochloric acid was added to adjust the pH in a range of 7–8, thus producing a bottom organic and a top aqueous phase. The organic phase was separated and distilled to give 19 g of the desired product, whose structure was confirmed by IR and NMR analysis.

The following dihydroperfluoroalkanols (Examples H2–H7) were synthesized using the same procedure as described in Example H1.

| Ex. | |
|---|---|
| H2. | $C_7F_{15}CF(CF_2CF_2CF_3)CH_2OH$ |
| H3. | $C_{10}F_{21}CF(CF_3)CH_2OH$ |
| H4. | $C_6F_{13}CF(CF_3)CH_2OH$ |
| H5. | $C_5F_{11}CF(CF_3)CH_2OH$ |
| H6. | $C_6F_{13}CF(CF_2CF_3)CH_2OH$ |
| H7. | $C_4F_9CF(CF_2CF_3)CH_2OH$ |

I. Synthesis and Evaluation of Polymers containing α-Branched Perfluoroalkyl Acrylates and Methacrylates Example I1

The homopolymer of $C_7F_{15}CF(CF_3)COOCH_2CH_2OCOCH=CH_2$ was prepared using the following procedure. A 100 mL 3-necked flask was charged with 10 g of neat $C_7F_{15}CF(CF_3)COOCH_2CH_2OCOCH=CH_2$ (the acrylate monomer from Example D1) and 0.2 g of azobis(isobutyronitrile) (AIBN). The flask was evacuated of air and was purged with nitrogen. The contents of the flask were heated to 60° C. with stirring for one hour to give the desired polyacrylate.

Examples I2–I4

In Examples I2–I4, homopolymers were made from the methacrylate monomers from Examples D8, D6 and D3 respectively using essentially the same procedure as was used to make the homopolymer from the monomer of Example D1. The homopolymers were evaluated for their glass transition temperatures according to Test Method ASTM E 1356-91, with results presented in Table 1.

TABLE 1

| Ex. | Mon. Ref | Monomer Structure | Tg (° C.) (bulk) | Tg (° C.) (sol'n) |
|---|---|---|---|---|
| I1. | D1 | $C_7F_{15}CF(CF_3)COOCH_2CH_2OCOCH=CH_2$ | 3 | −11 |
| I2. | D8 | $C_5F_{11}CF(CF_3)COOCH_2CH_2OCOC(CH_3)=CH_2$ | 16 | 2 |
| I3. | D6 | $C_6F_{13}CF(CF_3)COOCH_2CH_2OCOC(CH_3)=CH_2$ | 7 | −16 |
| I4. | D3 | $C_7F_{15}CF(CF_3)COOCH_2CH_2OCOC(CH_3)=CH_2$ | −3 | −22 |

The data in Table 1 show that both the acrylate and methacrylate hoimopolymers have relatively low glass transition temperatures.

Examples I5–I12

In Examples I5–I12, homopolymers were made from the acrylates and methacrylates from Examples D2, D3, D4, D5, D6, D8, D10 and D11 respectively using essentially the same procedure as was used to make the homopolymer from the monomer of Example D1. Each homopolymer was then dissolved in trifluorotoluene, coated onto a glass cover slip, and allowed to air-dry. After drying, aach coated slip was heat treated at 120° C. for 15 minutes to cure the polymer. Measurements of advancing contact angle with deionized water and n-hexadecane were then made on each polymer-coated glass cover slip using a Cahn Dynamic Contact Angle Analyzer, Model 322 (Wilhelmy balance and computer for control and data processing), with a stage speed of 150 microns per second. Contact angles are reported in Table 2 and are the average of 3 replicates.

TABLE 2

| | Mon. | | Contact Angle: | |
|---|---|---|---|---|
| Ex. | Ref. | Monomer Structure | Water | $C_{16}H_{34}$ |
| I5. | D2 | $C_8F_{17}CF(CF_3)COOCH_2CH_2OCOCH=CH_2$ | 111° | 78° |
| I6. | D3 | $C_7F_{15}CF(CF_3)COOCH_2CH_2OCOC(CH_3)=CH_2$ | 120° | 72° |
| I7. | D4 | $C_8F_{17}CF(CF_3)COOCH_2CH_2OCOC(CH_3)=CH_2$ | 112° | 74° |
| I8. | D5 | $C_6F_{13}CF(CF_3)COOCH_2CH_2OCOCH=CH_2$ | 119° | 72° |
| I9. | D6 | $C_6F_{13}CF(CF_3)COOCH_2CH_2OCOC(CH_3)=CH_2$ | 91° | 69° |
| I10 | D8 | $C_5F_{11}CF(CF_3)COOCH_2CH_2OCOC(CH_3)=CH_2$ | 113° | 70° |
| I11. | D10 | $C_{10}F_{21}CF(CF_3)COOCH_2CH_2OCOC(CH_3)=CH_2$ | 69° | 68° |
| I12. | D11 | $C_4F_9CF(CF_2CF_3)COOCH_2CH_2OCOC(CH_3)=CH_2$ | 95° | 69° |

The data in Table 2 show that excellent repellency to both aqueous and organic liquids is shown by each α-branched perfluoroalkyl-containing acrylate and methacrylate polymer, indicating that these polymers would be excellent repellents for fibrous substrates such as textiles, carpet and leather.

Example I13

A polymeric surfactant active in both organic solvents and water was made from $C_7F_{15}CF(CF_3)COOCH_2CH_2OCOCH=CH_2$, the acrylate monomer prepared in Example D1, using the following procedure. To an 8 ounce (225 mL) narrow mouth bottle were added 6.0 g of monomer D1, 28 g of 50% (wt) Pluronic™ L-44 diacrylate in toluene (prepared as described in Example 1 of U.S. Pat. No. 3,787,351 (Olson)), 0.8 g of mercaptopropanediol, 0.4 g of t-butyl peroctoate, and 113 g of isopropanol. The bottle with its contents was sealed and was tumbled at 90° C. for approximately 4–5 hours to polymerize the monomers. Then tumbling was ceased and the bottle was allowed to cool to room temperature before opening and admitting air. The resulting concentration of polymer was 15% by weight, as determined by evaporating a small weighed portion of the solution in a small dish in a forced air oven at 100° C. for 1 hour.

The polymer solution was diluted to 0.5% (wt) solids in both toluene and deionized water, and surface tension values of the diluted solutions, as measured using a Fisher Model 20 duNuoy Tensiometer, were found to be 25.7 dynes/cm in toluene and 21.3 dynes/cm in water.

Example I14

A waterborne copolymer was prepared from an α-branched perfluoroalkylcarbonyl-derived acrylate by the following procedure. To a 16 oz (225 mL) bottle was charged 36 g of $C_8F_{17}CF(CF_3)COOCH_2CH_2OCOCH=CH_2$ (from Example D2), 15 g of acrylic acid, 2.5 g of $CH_2=C(CH_3)COOCH_2CH_2Si(OCH_3)_2$, 40 g of isopropanol, 20 g of N-methylpyrrolidinone and 0.40 g of AIBN. The charged bottle was purged with nitrogen for about 5 minutes, the bottle was sealed, and the contents were allowed to polymerize at 80° C. for 5 hours. The polymer formed was transferred to a flask and isopropanol was stripped at 70° C. under reduced pressure. The polymer was then neutralized by dispersing into 150 g of 2.4% (wt) aqueous ammonium hydroxide. The solids content of this solution was 16.2% by weight, measured by evaporating a small sample at 80° C. for 2 hours.

To 50 g of the above-made solution was added 41 g of CX-WS-300 crosslinker (a 10% aqueous dispersion of an oxazoline terpolymer made from 85% isopropenyl oxazoline, 10% methyl methacrylate and 5% ethyl methacrylate; commercially available from Nippon Shokubai, Japan), and the pH of the formulation was adjusted to 7.5 by the addition of a very small amount of aqueous ammonia. This formulation was then aged for 1 week at room temperature, after which a small sample was coated into clear polyethylene terephthalate (PET) film using a #15 wire-wound rod. The coated PET film was cured for 10 minutes at 120° C., producing a transparent coating which caused dewetting of ink applied to the coated film from a blue Sharpie™ permanent marker.

J. Synthesis of Nonionic Surfactant Containing α-Branched Perfluoroalkyl Group

Example J1

$C_8F_{17}CF(CF_3)CO(OCH_2CH_2)_{16}OCH_3$ was prepared using the following procedure. An equimolar mixture of $C_8F_{17}CF(CF_3)COF$ (from Example A7) and Carbowax™ 750 methoxy-terminated diol (commercially available from Union Carbide Corp., Danbury, Conn.) were reacted for 5 hours in stirred refluxing tetrahydrofuran (THF). The THF was then removed under reduced pressure to give the desired nonionic surfactant, whose structure was confirmed using IR analysis.

K. Synthesis of Amphoteric Surfactants Containing α-Branched Perfluoroalkyl Groups

Example K1

$C_7F_{15}CF(CF_3)CONH(CH_2)_3N^+(CH_3)_2C_2H_4COO^-$ was prepared using the following procedure. 12.0 g (0.02 mol) of the amidoamine intermediate of Example B1 and 1.66 g (0.023 mol) of acrylic acid were added to a round bottom flask, and the resulting mixture was stirred at room temperature for 6 days to obtain a viscous amber liquid. The completion of reaction was confirmed by dissolving 1% by weight of the amber liquid in deionized water and adjusting the pH of the resulting solution to 8 using dilute aqueous NaOH. The solution stayed clear with no precipitate of amidoamine starting material evident, indicating good completion of reaction to form the desired product, $C_7F_{15}CF(CF_3)CONH(CH_2)_3N^+(CH_3)_2C_2H_4COO^-$. 1H NMR spectroscopy was consistent with the desired product.

Example K2

21.9 g (0.04 mol) of the amidoamine intermediate of Example B3 and 4.9 g (0.04 mol) of γ-propane sultone were added to a 3-necked round bottom flask equipped with a stirrer and thermometer. The mixture was heated to 80° C. with stirring, when an exotherm to 135° C. occurred. The temperature was kept at 135° C. for 15 minutes, then the contents of the flask were allowed to cool at room temperature. Upon cooling, 26.8 g of a cream-colored solid formed which was broken up with a spatula. The completion of reaction was confirmed by dissolving a small amount of the solid in deionized water and raising the pH of the resulting aqueous solution to 8 using dilute aqueous NaOH. The solution stayed clear with no precipitate of the amidoamine intermediate evident, indicating good completion of reaction. Analysis by infrared and $^1H$ NMR spectroscopy confirmed the product to be primarily a mixture of the amphoteric surfactants $C_6F_{13}CF(CF_3)CON(C_3H_6SO_3^-)(CH_2)_3N^+(CH_3)_2H$ and $C_6F_{13}CF(CF_3)CONH(CH_2)_3N^+(CH_3)_2C_3H_6SO_3^-$ The following acrylic acid adducts (Examples K3 and K4) were synthesized using an analogous procedure as described in Example K1, except that amidoamine of Examples B14 and B15 respectively were substituted for the amidoamine of Example B1.

| Ex. | |
|---|---|
| K3. | 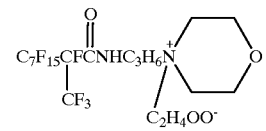 |
| K4. | 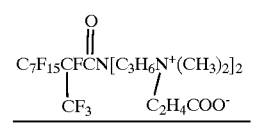 |

Evaluation of α-Branched Perfluoroalkyl Surfactants

The α-branched perfluoroalkyl surfactants made in several of the previous examples were dissolved in deionized water at various concentrations and the surface tension of each resulting aqueous surfactant solution was measured using a K-12 Processor Tensiometer and 665 Dosimat™ measuring method. Then the critical micelle concentration (CMC) was determined for each surfactant. The CMC for each surfactant and the corresponding surface tension at the CMC are presented in Table 3.

TABLE 3

| From Ex.: | Salt Structure | Surf Tens. (dynes/cm) | CMC (ppm) |
|---|---|---|---|
| E2 | $C_5F_{11}CF(CF_3)CONH(CH_2)_3N^+(CH_3)_2O^-$ | 17.5 | 500 |
| E3 | $C_6F_{13}CF(CF_3)CONH(CH_2)_3N^+(CH_3)_2O^-$ | 16.6 | 100 |
| E1 | $C_7F_{15}CF(CF_3)CONH(CH_2)_3N^+(CH_3)_2O^-$ | 16.3 | 20 |
| E4 | $C_8F_{17}CF(CF_3)CONH(CH_2)_3N^+(CH_3)_2O^-$ | 16.5 | 20 |
| E5 | $C_{10}F_{21}CF(CF_3)CONH(CH_2)_3N^+(CH_3)_2O^-$ | 17.1 | 500 |
| E7 | $C_7F_{15}CF(C_3F_7)CONH(CH_2)_3N^+(CH_3)_2O^-$ | low solub. | — |
| E8 | $C_7F_{15}CF(CF_3)CON(C_2H_4OH)(CH_2)_3N^+(CH_3)_2O^-$ | 16.6 | 125 |
| E9 | $C_7F_{15}CF(CF_3)CONHC_3H_6$-N⁺(morpholine N-oxide) | low solub. | — |
| E11 | $C_6F_{13}CF(CF_3)COOC_2H_4NHC(O)$-pyridine N-oxide | 15.5 | 1000 |
| E10 | $C_7F_{15}CF(CF_3)COOC_2H_4NHC(O)$-pyridine N-oxide | 14.5 | 400 |
| E12 | $C_6F_{13}CF(CF_3)COOC_2H_4$-pyridinium N-oxide | 18.3 | 8000 |
| E13 | $C_7F_{15}CF(CF_3)COOC_2H_4$-pyridinium N-oxide | 15.0 | 6000 |
| F8 | $C_7F_{15}CF(CF_3)CON[(CH_2)_3N^+(CH_3)_2H]_2\ 2\ OAc^-$ | 22.0 | 1000 |
| F7 | $C_5F_{11}CF(CF_3)COO(CH_2)_3N^+(CH_3)_2H\ ^-OOCCH_2C(OH)(COOH)CH_2COOH$ | 17.0 | 1000 |
| F3 | $C_5F_{11}CF(CF_3)CONH(CH_2)_3N^+(C_2H_4OH)(CH_3)_2\ Cl^-$ | 17.0 | 1000 |
| F4 | $C_7F_{15}CF(CF_3)CONH(CH_2)_3N^+(C_2H_4OH)(CH_3)_2\ Cl^-$ | 19.0 | 300 |
| F9 | $C_7F_{15}CF(CF_3)CN[C_3H_6N^+(C_2H_4OH)(CH_3)_2]_2\ 2Cl^-$ | 22.0 | 1000 |
| F6 | $C_7F_{15}CF(CF_3)CONHC_3H_6N^+$-morpholine $^-OOCCH_3$ | 18.6 | 1000 |

TABLE 3-continued

| From Ex.: | Salt Structure | Surf Tens. (dynes/cm) | CMC (ppm) |
|---|---|---|---|
| F2 | $C_6F_{13}CF(CF_3)COOC_2H_4NHC(O)$-pyridinium-$CH_3$ $I^-$ | 15.5 | 30 |
| F1 | $C_7F_{15}CF(CF_3)COOC_2H_4NHC(O)$-pyridinium-$CH_3$ $I^-$ | 15.0 | 500 |
| F5 | $C_7F_{15}CF(CF_3)CNHC_3H_6N^+$-morpholino-$C_2H_4OH$ $Cl^-$ | 20.8 | 1000 |
| K1 | $C_7F_{15}CF(CF_3)CONH(CH_2)_3N^+(CH_3)_2C_2H_4COO^-$ | 16.6 | 125 |
| K2 | $C_6F_{13}CF(CF_3)CON(C_3H_6SO_3^-)(CH_2)_3N^+(CH_3)_2H$ | 20.3 | 500 |
| K3 | $C_7F_{15}CF(CF_3)CNHC_3H_6N^+$-morpholino-$C_2H_4COO^-$ | 19.2 | 1000 |
| K4 | $C_7F_{15}CF(CF_3)CN[C_3H_6N(CH_3)_2]_2 \cdot C_2H_4COO^-$ | 23.6 | 100 |
| J1 | $C_8F_{17}CF(CF_3)CO(OCH_2CH_2)_{16}OCH_3$ | 22 | 150 |

The data in Table 3 show that the α-branched perfluoroalkyl surfactants exhibit good surface tension reduction in water, with especially good results shown by the amine oxides and pyridinium iodides.

L. Evaluation of α-Branched Perfluoroalkylcarbonyl Amine Oxide Surfactants in AFFF Formulations Example L1

In Example L1, a 3% AFFF concentrate was formulated as follows:

| 3% AFFF Concentrate (% solids by weight): | |
|---|---|
| 1.5% | fluorinated amine oxide surfactant E1, $C_7F_{15}CF(CF_3)CONHCH_2CH_2CH_2N^+(CH_3)_2O^-$ |
| 2.0% | sodium n-octyl sulfate (Sipex ™ OLS) |
| 3.0% | sodium cocoampho propionate (Miranol ™ C2M-SF) |
| 25.0% | dipropylene glycol n-propyl ether |
| 68.5% | deionized water and surfactant co-solvents |

(pH of concentrate was adjusted to around 8.3 using glacial acetic acid)

Three parts by volume of the resulting concentrate was diluted each with 97 parts by volume of fresh water and synthetic sea water (ASTM D1141-52) to form 3% premixes which were evaluated for AFFF performance using the following test methods: Foam Expansion and Drain Time, Film-Formation and Sealability, Surface Tension and Interfacial Tension. Results from the 3% premix evaluations are presented in Table 4.

TABLE 4

| Test Method | 3% tap | 3% sea | Spec. |
|---|---|---|---|
| Foam Expansion | 8.2 | 7.8 | >5.0 |
| 25% Drain Time | 204 | 202 | >150 |
| Film Formation & Sealability | pass | pass | pass |
| Extinguishment Time | 40 | 40 | <50 |
| 25% Burnback Time | 410 | 369 | >360 |

The data in Table 4 show that an excellent AFFF 3% concentrate can be made by incorporating an α-branched perfluoroalkylcarbonyl amine oxide surfactant in the concentrate at only 1.5% by weight.

M. Synthesis and Evaluation of α-Branched Perfluorocarboxylic Acids and α-Branched Perfluorocarboxylate Salts Example M1

$C_7F_{15}CF(CF_3)COOH$ was prepared by the hydrolysis of $C_7F_{15}CF(CF_3)COF$ (from Example A1) using the following procedure. 860 g of $C_7F_{15}CF(CF_3)COF$ was stirred with 3000 mL of deionized water for 6 hours at room temperature. Concentrated hydrochloric acid was added to obtain a phase split. The bottom layer was separated and the resulting crude acid was purified by distillation under reduced pressure (120–125° C./2 torr). 770 g of acid was received as a white solid after cooling to room temperature. The structure of the acid was confirmed using $^{19}$F NMR analysis.

Examples M2–M7

The following α-branched perfluorocarboxylic acids (Examples M2–M9) were prepared from various α-branched perfluoroalkylcarbonyl fluorides using the same procedure as described in Example M1.

| Ex. | Perfluorocarboxylic Acid |
|---|---|
| M2. | $C_5F_{11}CF(CF_3)COOH$ |
| M3. | $C_6F_{13}CF(CF_3)COOH$ |
| M4. | $C_6F_{13}CF(C_2F_5)COOH$ |
| M5. | $C_7F_{15}CF(C_3F_7)COOH$ |
| M6. | $C_8F_{17}CF(CF_3)COOH$ |
| M7. | $C_{10}F_{21}CF(CF_3)COOH$ |
| M8. | $C_4F_9CF(C_2F_5)COOH$ |
| M9. | $C_6F_{13}CF(C_4F_9)COOH$ |

Example M10

$C_7F_{15}CF(CF_3)COO^- H_4N^+$ was prepared by neutralizing $C_7F_{15}CF(CF_3)COOH$ (from Example M1) with ammonia using the following procedure. 300 g of $C_7F_{15}CF(CF_3)COOH$ was dissolved in 500 mL of Fluorinert™ FC-77 Electronic Liquid (commercially available from 3M Company, St. Paul, Minn.) at room temperature. A stoichiometric amount of anhydrous ammonia gas was passed through the solution, gradually forming a white precipitate. Following neutralization, the solvent was removed under reduced pressure and the resulting white solid was dried under ambient conditions.

Examples M11–M13

Using the same procedure as described in Example M10, the following ammonium carboxylate salts were prepared.
M11. $C_6F_{13}CF(CF_3)COO^- H_4N^+$
M12. $C_8F_{17}CF(CF_3)COO^- H_4N^+$
M13. $C_6F_{13}CF(C_2F_5)COO^- H_4N^+$ Example M14

$C_7F_{15}CF(CF_3)COO^- H_4N^+$ was prepared from the free acid using the following procedure. An aqueous dispersion of $C_7F_{15}CF(CF_3)COOH$ (from Example M1) was neutralized with a stoichiometric amount of concentrated aqueous ammonium hydroxide (28–30%) at room temperature and with mixing, resulting in the formation of an aqueous solution of $C_7F_{15}CF(CF_3)COO^- H_4N^+$. The aqueous solution was dried under ambient conditions to give the desired ammonium salt as a white solid.

Examples M15–M27

The following a-branched perfluorocarboxylate salts (Examples M15–M27) were synthesized from their α-branched perfluorocarboxylic acid analogues (Examples M1–M9) using the same neutralization procedure as described in Example M14 and keeping the molar ratio of reactants the same, except that the base was varied, using either ammonium hydroxide, ethanolamine, potassium hydroxide, sodium hydroxide or lithium hydroxide.

| Ex. | Perfluoroalkyl Carboxylic Acid/Salt |
|---|---|
| M15. | $C_5F_{11}CF(CF_3)COO^- H_4N^+$ |
| M16. | $C_6F_{13}CF(CF_3)COO^- H_4N^+$ |
| M17. | $C_8F_{17}CF(CF_3)COO^- H_4N^+$ |
| M18. | $C_{10}F_{21}CF(CF_3)COO^- H_4N^+$ |
| M19. | $C_6F_{13}CF(C_2F_5)COO^- H_4N^+$ |
| M20. | $C_7F_{15}CF(CF_3)COO^- H_3N^+C_2H_4OH$ |
| M21. | $C_5F_{11}CF(CF_3)COO^- K^+$ |
| M22. | $C_6F_{13}CF(CF_3)COO^- K^+$ |
| M23. | $C_7F_{15}CF(CF_3)COO^- K^+$ |
| M24. | $C_8F_{17}CF(CF_3)COO^- K^+$ |
| M25. | $C_6F_{13}CF(CF_3)COO^- Na^+$ |
| M26. | $C_7F_{15}CF(CF_3)COO^- Na^+$ |
| M27. | $C_7F_{15}CF(CF_3)COO^- Li^+$ |
| M28. | $C_5F_{11}CF(CF_3)COO^- Na^+$ |
| M29. | $C_6F_{13}CF(C_4F_9)COO^- H_4N^+$ |

Example M30

$C_7F_{15}CF(CF_3)COO^-$ ½$[H_3N^+C_2H_4NHC_2H_4N^+H_3]$ was prepared from the free acid using the following procedure. 4.0 g (7.78 mmol) of $C_7F_{15}CF(CF_3)COOH$ (from Example M1), 0.40 g (3.89 mmol) of diethylenetriamine, and 82.6 g of deionized water were combined, warmed to 60° C. and cooled, resulting in a white pasty dispersion solution containing 5.06% (wt) solids of the desired polyammonium perfluorocarboxylate salt.

The carboxylate salts from Examples M14–M30 were dissolved in deionized water at various solids concentrations and the surface tension of each resulting aqueous surfactant solution was measured. Then the critical micelle concentration (CMC) was determined for each surfactant. The CMC for each surfactant and the corresponding surface tension at the CMC are presented in Table 5. Also presented in Table 5 for comparison is the surface tension value measured for Fluorad™ FC-143 Fluorochemical Surfactant, a perfluorocarboxylate ammonium salt of structure $C_7F_{15}COO^- H_4N^+$, containing predominantly linear perfluoro groups and essentially free from a-branching (commercially available from 3M Company, St. Paul Minn.).

TABLE 5

| From Ex. | Salt Structure | Surf. Tens. (dynes/cm) | CMC (ppm) |
|---|---|---|---|
| M15 | $C_5F_{11}CF(CF_3)COO^- H_4N^+$ | 22.1 | >10000 |
| M21 | $C_5F_{11}CF(CF_3)COO^- K^+$ | 22.5 | >10000 |
| M16 | $C_6F_{13}CF(CF_3)COO^- H_4N^+$ | 17.9 | 8000 |
| M22 | $C_6F_{13}CF(CF_3)COO^- K^+$ | 17.5 | 10000 |
| M25 | $C_6F_{13}CF(CF_3)COO^- Na^+$ | 19.8 | 10000 |
| M14 | $C_7F_{15}CF(CF_3)COO^- H_4N^+$ | 16.5 | 2500 |
| M20 | $C_7F_{15}CF(CF_3)COO^- H_3N^+C_2H_4OH$ | 15.0 | 500 |
| M23 | $C_7F_{15}CF(CF_3)COO^- K^+$ | 15.0 | 2500 |
| M26 | $C_7F_{15}CF(CF_3)COO^- Na^+$ | 19.4 | 3000 |
| M27 | $C_7F_{15}CF(CF_3)COO^- Li^+$ | 24.1 | 3500 |
| M17 | $C_8F_{17}CF(CF_3)COO^- H_4N^+$ | 14.7 | 2300 |
| M24 | $C_8F_{17}CF(CF_3)COO^- K^+$ | 16.4 | 3000 |
| M18 | $C_{10}F_{21}CF(CF_3)COO^- H_4N^+$ | 14.8 | 600 |
| M30 | $C_7F_{15}CF(CF_3)COO^-$ ½ $[H_3N^+C_2H_4NHC_2H_4N^+H_3]$ | 16.2 | 3000 |
| FC-143 | $C_7F_{15}COO^- H_4N^+$ | 21.5 | 8000 |

The data in Table 5 show that the a-branched perfluorocarboxylate salts of this invention demonstrated excellent surface tension depression in water. Lower values of both surface tension and CMC were achieved with longer $R_f$ chain salts. Also, lower surface tension values were obtained with ammonium, polyammonium and potassium salts as compared to sodium and lithium salts. Surface tensions imparted by the α-branched perfluorocarboxylate ammonium salts were lower than the surface tension demonstrated by FC-143, the primarily straight chain perfluorocarboxylate ammonium salt. Due to their excellent surface properties, it is expected that the α-branched perfluorocarboxylate salts of this invention would make excellent biodegradable replacements for the straight chain branched perfluorocarboxylate salts now used commercially as fluoropolymer emulsifiers.

N. Degradation Measurements of α-Branched Perfluoroalkylcarbonyl Derivatives

Example N1

The thermal degradation of an aqueous a-branched perfluoroalkylcarbonyl fluoride and the characterization of the products produced from the degradation were carried out using the following procedure. 8 g of $C_7F_{15}CF(CF_3)COF$ (made as in Example A4) was dispersed in deionized water and was refluxed for 2 hours. 5.7 g of volatile degradation products were then collected by azeotropic distillation using a Dean-Stark apparatus. The structures of the products and their amounts, as determined by $^{19}F$ NMR and GC spectra analysis, were 85% monohydride, $C_7F_{15}CFHCF_3$, and 15% olefin, $C_6F_{13}CF=CFCF_3$ (a mixture of cis- and trans-isomers). No volatile products were formed when $C_7F_{15}CF(CF_3)COF$ was replaced with n-$C_7F_{15}COF$, a non-α-branched perfluoroalkylcarbonyl fluoride, made by electrochemical fluorination of n-$C_7H_{15}COF$.

The thermal degradation of $C_7F_{15}CF(CF_3)COF$ (from Example A4) dispersed in water was also carried out by heating the aqueous mixture for several hours at approximately 80° C. The same volatile products were formed as in Example N1 and were collected by phase separation followed by distillation.

The thermal degradation of $C_7F_{15}CF(CF_3)COOH$ (from Example L1) in aqueous solution was carried out in a similar way to give the same monohydride and olefin.

Examples N2–N9

Thermal degradation measurements were made on a series of neat perfluorocarboxylate salts, including several ax-branched open chain structures (Examples N2–N9), a primarily linear open chain structure (Example N10—Fluorad™ FC-143 Fluorochemical Surfactant, commercially available from 3M Company, St. Paul, Minn.), and a closed chain (i.e., cyclic) structure (Example N11—made by the electrochemical fluorination of benzoic acid and hydrolysis in the presence of KOH, as described in U.S. Pat. No. 2,567,011 (Diesslin et al.)).

The perfluorocarboxylate salts were tested using a Perkin-Elmer TGA 7 thermogravimetric analysis apparatus and a salt sample size of approximately 5 mg, a heating rate of 10° C./min, and a nitrogen gas flow rate of 40–45 mL/min. Using the TGA 7 software, the following temperatures were recorded: (1) the onset temperature of decomposition, (2) the temperature at which 50% of the sample weight was lost, and (3) the temperature at which 90% of the sample weight was lost. Results of these thermal degradation experiments are presented in Table 6.

TABLE 6

| Ex. | Acid Salt Structure (Reference) | Onset | 50% loss | 90% loss |
|---|---|---|---|---|
| | | \multicolumn{3}{c}{Temperature (° C.) for:} | | |
| N2. | $C_5F_{11}CF(CF_3)COO^-NH_4^+$ (Ex. M15) | 166 | 178 | 188 |
| N3. | $C_6F_{13}CF(CF_3)COO^-NH_4^+$ (Ex. M16) | 165 | 179 | 193 |
| N4. | $C_7F_{15}CF(CF_3)COO^-NH_4^+$ (Ex. M14) | 151 | 163 | 174 |
| N5. | $C_8F_{17}CF(CF_3)COO^-NH_4^+$ (Ex. M17) | 142 | 162 | 184 |
| N6. | $C_{10}F_{21}CF(CF_3)COO^-NH_4^+$ (Ex. M18) | 164 | 181 | 188 |
| N7. | $C_6F_{13}CF(C_2F_5)COO^-NH_4^+$ (Ex. M19) | 153 | 171 | 188 |
| N8. | $C_5F_{11}CF(CF_3)COO^-Na^+$ (Ex. M28) | 236 | 250 | 263 |
| N9. | $C_5F_{11}CF(CF_3)COO^-K^+$ (Ex. M21) | 167 | 178 | 188* |
| FC-143 | $C_7F_{15}COO^-NH_4^+$ (FC-143) | 173 | 188 | 202 |
| U.S. Pat. No. 2,567,011 | (perfluorocyclohexyl)-$COO^-K^+$ | 100 | 110 | 120 |

*Stopped at 85% weight loss as remaining salt, KF, is not volatile

The data in Table 6 show that, when thermally degraded as neat salts, the temperatures at which the α-branched open chain structures decomposed were only slightly lower than the temperatures at which the primarily linear open chain structure decomposed. This is in marked contrast to Example N1 where, in aqueous media, the α-branched open chain structures decomposed at far lower temperatures than did the primarily linear open chain structure. The neat closed chain perfluorocyclohexyl structure decomposed at a significantly lower temperature than did either the α-branched or primarily linear open chain structures.

Example N10

The α-branched open chain ammonium salt compounds from Examples N3-N6 were dissolved in deionized water at a concentration of 5% by weight (0.5 g ammonium salt in 10 mL water) and were stored at room temperature. Many structures showed about 20–30% degradation after 1 year.

An aqueous solution of $C_7F_{15}COO^-\ NH_4^+$ (FC-143), which is primarily linear, would show no signs of degradation over the same 1 year time period.

Example N11

The environmental stability of $C_6F_{13}CF(CF_3)COO^-NH_4^+$ was investigated under ambient conditions using a bacterial sludge contact test. In this test, bacterial sludge was obtained from the municipal waste treatment plant at Pig's Eye, Minn., the sludge was centrifuged to collect the water-insoluble high density solids, and was reconstituted in water to a standard level of about 2000 ppm of total suspended solids. A 5 mL aliquot of the 2000 ppm sludge in water was placed in each of several 20 mL vials, and enough of the carboxylate salt was added to each vial to achieve a concentration of about 496 ppm (1 millimolar). Each vial was tightly capped with a septum cap and was allowed to stand at room temperature. At intervals, the concentrations of perfluoroolefin and perfluoromonohydride gases in each headspace were measured by removing a gas sample from the space over the liquid, using a Hewlitt Packard Gas Chromatograph with a headspace sampling accessory. The peak areas determined from each gas sample were compared to a standard series made by placing increasing concentrations of a defined mixture of perfluoroolefin and perfluoromonohydride in water in the same types of vials, and subjecting the headspaces in the vials to the same analytical procedure. Results, given below, state the complete conversion relative to theoretical percent of the amount of perfluoroolefin/perfluoromonohydride mixture formed relative to that expected from complete conversion of the salt to volatile fluorocarbons. A control experiment using water with no sludge was also run at the 28 day test point.

% Perfluoroolefin/Perfluoromonohydride Formed after:

Day 1-4%

Day 4-13%

Day 7-23%

Day 14-44%

Day 28-70%

Day 28 (no sludge)-32%

The data supra show that, after 28 days at ambient conditions, the presence of the sludge more than doubled the amount of perfluoroolefin/perfluoromonohydride mixture produced.

O. Toxicity Measurements of α-Branched Perfluorocarboxylate Salts

Example O1

Acute $LD_{50}$ measurements for a one-time feeding study of rats were determined over a 21 day period for both the a-branched perfluorocarboxylate salt, $C_7F_{15}CF(CF_3)COO^- NH_4^+$, and its straight chain isomer, $CF_3(CF_2)_8COO^-NH_4^+$.

The $LD_{50}$ value for $C_7F_{15}CF(CF_3)COO^- NH_4^+$ was determined to be in the range of 500–1000 mg/kg, which is only slightly toxic. No wasting syndrome was noted as deaths from toxic doses occurred within 2–3 days. Rats began regaining weight after 3 days.

The $LD_{50}$ value for $C_9F_{19}COO^- NH_4^+$ was determined to be in the range of 50–100 mg/kg (ca. 10 times as toxic as the α-branched isomer), which is moderately toxic. Wasting syndrome was observed in affected animals.

Example O2

Additional biological testing of $C7F_{15}CF(CF_3)COO^- NH_4^+$ in rats was conducted using the following test apparatus. An uptake desiccator jar chamber was designed with top and bottom portions, the top portion equipped with an inlet port, an outlet port, oxygen monitor and pressure gage. An oxygen gas tank supplied oxygen into the inlet port, and the oxygen level in the chamber was maintained at a normal ambient level as measured by the oxygen monitor and pressure gage. The outlet port was connected in series with a carbon dioxide scrubber and particulate filter, which in turn was connected to a loop containing a stainless steel bellows pump operating at about 2 L/min. Most of the gas in the loop was recycled into the inlet port, but about 100 mL/min was directed through a secondary loop to a gas chromatograph equipped with a 0.5 mL gas sampling loop.

A rat dosed at 500 mg/kg was placed in the bottom portion of the chamber, the top portion was attached, and the assembled chamber was placed in an ice-filled pan to allow for the condensation of water. The oxygen flow was started, and the exhaust gases were monitored for the presence of $CF_3CF=CF(C_6F_{13})$ and $C_7F_{15}CFHCF_3$, aqueous degradation products of $C_7F_{15}CF(CF_3)COOH$, using known standards of this olefin and hydride in the gas chromatograph. Initially, no olefin or hydride were detected in the exhaust gases. After 24 minutes, one slight chromatographic peak was noted, corresponding to the monohydride. After 92 minutes, the peak became noticeably larger and a second peak formed, corresponding to the olefin. After 217 minutes, both peaks became significantly larger. Post-exposure observation noted no evidence of toxicity (death) or evidence of wasting syndrome; this reduced toxicity was probably attributable to α-branching and not decarboxylation and elimination of the material.

This experiment demonstrated that the a-branched perfluorocarboxylate salt was being metabolized by the rat to volatile metabolites which were eliminated from the rat via transpiration. This study documents a significant biological elimination pathway for the α-branched material that is not present for the straight-chain analogs. This pathway, involving gaseous exchange at the bload-air barrier in the lungs, should be applicable for most other air-breathing animals, including humans.

P. Use of Surfactants in Emulsion Polymerization

Example P1

The following procedure was used to evaluate $C_7F_{15}CF(CF_3)COO^- NH_4^+$ (from Ex. M1) as an emulsifier to copolymerize hexafluoropropylene (HFP) and vinylidene fluoride.

A 1 gallon, vertically agitated stainless steel reactor with pressure and temperature controls was evacuated and twice purged with nitrogen. Using an isolated vacuum, a solution comprised of 2 g of ammonium persulfate (initiator) and 6 g of dipotassium phosphate dissolved in 2800 g of deionized water was introduced into the reactor. The remaining vacuum on the reactor was vented with nitrogen, and the solution was degassed twice under agitation using alternate vacuum and nitrogen purges. A sufficient amount of a solution of $C_7F_{15}CF(CF_3)COO^- NH_4^+$ in approximately 20 g of 60–70° C. deionized water was introduced to the reactor under isolated vacuum to give a calculated final concentration of 350 ppm emulsifier in the aqueous solution. The reactor was vented with nitrogen, the solution was agitated very briefly, and the reactor was evacuated of nitrogen and isolated. Then the reactor was vented with hexafluoropropylene monomer to a pressure of approximately 10 psig (1280 torr total pressure), and the temperature of the batch was raised to 72° C. with high agitation. Maintaining the temperature at 72° C., a monomer mixture of 60% (wt) of vinylidene fluoride and 40% (wt) hexafluoropropylene was fed from a tared gas cylinder into the head space of the reactor to maintain a reactor pressure of 130 psig (7480 total pressure). After feeding in about 1 kg of monomer blend (approximately 3.75 hours duration), the introduction of monomer was ceased, the reaction was allowed to cool to room temperature, and any residual unreacted monomer was vented.

The resulting latex polymer was drained from the reactor, and percent solids of the latex was determined to be 25% by weight as measured by drying 10 g of latex in a forced air oven for 16 hours at 105° C.

The reactor body was separated from the reactor head, and a visual inspection of the reactor was made to determine the amount of coagulated polymer in the reactor (the amount should be minimal in a good polymerization reaction). A qualitative rating was assessed, ranging from "none" to "little" to "some."

The latex stability was determined by half filling a 16 oz (450 mL) jar with latex and shaking several hours in the horizontal position, quantitatively rating the latex after shaking using a 3-point scale ranging from 0=very stable to 3=unstable.

Particle size in the latex was determined using 900 scattering on a Coulter sub-micron particle size analyzer.

Degree of foaming was rated using the following qualitative scale: 0=not foamy, 1=slightly foamy, 2=moderately foamy, and 3=very foamy.

Example P2

In Example P2, the same experiment was run as in Example P1, except that the concentration of $C_7F_{15}CF(CF_3)COO^- NH_4^+$ emulsifier was raised to 3500 ppm, the reaction time decreased from 3.75 to 3.5 hours, and the reaction temperature increased from 72° C. to 78° C.

Comparative Examples P3–P7

In Comparative Examples P3–P6, the same experiment was run as in Example P1, except that $C_8F_{17}SO_2N(C_2H_5)CH_2COO^- K^+$ (Fluorad™ FC-128 Fluorochemical Surfactant, available from 3M Company, St. Paul, Minn.), $C_7F_{15}COO^-H_4N^+$ (Fluorad™ FC-143 Fluorochemical Surfactant), and Surflon™ S111S Fluorochemical Surfactant (believed to be nominally telomer-based n-$C_9F_{19}COO^-H_4N^+$, commercially available from Asahi Glass Corp., Japan) were substituted for $C_7F_{15}CF(CF_3)COO^-H_4N^+$ emulsifier.

In Comparative Example P7, the same experiment was run as in Example P1, except that no emulsifier was used.

Reaction conditions and results for all fluoropolymer experiments are presented in Table 7.

TABLE 7

| Ex. | Emulsifier | Conc. ppm | Temp (° C.) | Time (hrs) |
|---|---|---|---|---|
| P1. | $C_7F_{15}CF(CF_3)COO^-NH_4^+$ | 350 | 72 | 3.75 |
| P2. | $C_7F_{15}CF(CF_3)COO^-NH_4^+$ | 3500 | 78 | 3.5 |
| P3. | Fluorad ™ FC-128 | 100 | 72 | 4.5 |
| P4. | Fluorad ™ FC-128 | 350 | 72 | 4 |
| P5. | Fluorad ™ FC-143 | 350 | 74 | 4 |
| P6. | Surflon ™ S111S | 350 | 72 | 3.75 |
| P7. | none | — | 76 | 3.25 |

| Ex. | Emulsifier | Size (nm) | Foaming | Coagulation | Latex Stability |
|---|---|---|---|---|---|
| P1. | $C_7F_{15}CF(CF_3)COO^-NH_4^+$ | 210 | 2 | some | 2 |
| P2. | $C_7F_{15}CF(CF_3)COO^-NH_4^+$ | 69 | 1 | none | 0 |
| P3. | Fluorad ™ FC-128 | 237 | 2 | some | 2 |
| P4. | Fluorad ™ FC-128 | 88 | 2 | none | 0 |
| P5. | Fluorad ™ FC-143 | 209 | 3 | some | 2 |
| P6. | Surflon ™ S111S | 203 | 2–3 | some | 2 |
| P7. | none | 233 | 0 | some | 3 |

The data in Table 7 show that at the lower concentration (350 ppm), $C_7F_{15}CF(CF_3)COO^- NH_4^+$ performs comparably to Fluorad™ FC-143 and Surflon™ S111S, both commercially available fluorochemical surfactants frequently used as fluoropolymer emulsifiers, in creating small particle size with no coagulation but with less foaming. At the higher concentration (3500 ppm) of $C_7F_{15}CF(CF_3)COO^- NH_4^+$, particle size was reduced from 210 nm to 69 nm, foaming was lowered (from "2" to "1" on a 3-point scale) and coagulation was eliminated, with overall performance being comparable to Fluorad™ FC-128.

We claim:

1. An aqueous film-forming foamable composition comprising one or more surfactants of the formula

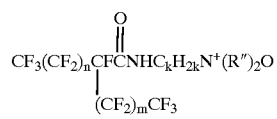

wherein
n is between 4 and about 18 inclusive;
m is between 0 and about 9 inclusive;
k is between 2 and 6 inclusive; and
R" is a lower alkyl group having from 1 to 4 carbon atoms or may combine with the depicted nitrogen atom to from a pyridinyl, piperidino or morpholino heterocyclic ring.

2. The composition of claim 1 comprising one or more surfactants of the formula:

$C_5F_{11}CF(CF_3)CONH(CH_2)_3N^+(CH_3)_2O^-$
$C_6F_{13}CF(CF_3)CONH(CH_2)_3N^+(CH_3)_2O^-$
$C_6F_{13}CF(C_2F_5)CONH(CH_2)_3N^+(CH_3)2O^-$
$C_7F_{15}CF(CF_3)CONH(CH_2)_3N^+(CH_3)_2O^-$
$C_7F_{15}CF(CF_3)CON(C_2H_4OH)(CH_2)_3N^+(CH_3)_2O^-$
$C_7F_{15}CF(C_3F_7)CONH(CH_2)_3N^+(CH_3)_2O^-$
$C_8F_{17}CF(CF_3)CONH(CH_2)_3N^+(CH_3)_2O^-$
$C_{10}F_{21}CF(CF_3)CONH(CH_2)_3N^+(CH_3)_2O^-$
$C_7F_{15}CF(CF_3)CON[(CH_2)_3N^+(CH_3)_2O^-]_2$

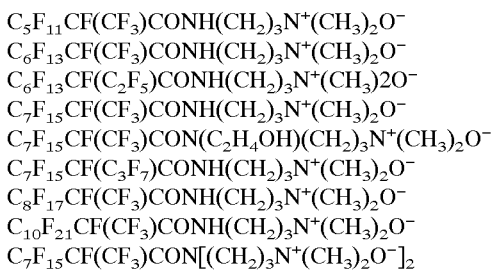

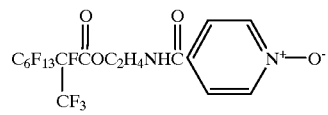

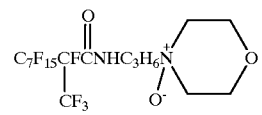

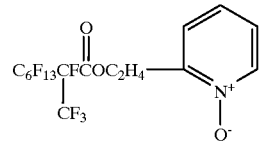

and

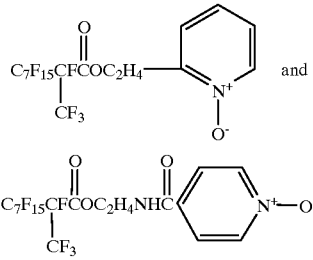

3. The composition of claim 1 further comprising one or more fluorine-free surfactants selected from the group of nonionic surfactants having a hydrophilic-lipophilic balance of greater than or equal to about 10; anionic surfactants having a carbon chain length of 6 to 16 inclusive; and amphoteric surfactants.

4. The composition of claim 3 wherein said fluorine-free surfactant comprises from 1 to about 30 percent by weight of said composition.

5. The composition of claim 1 wherein said surfactant comprises 1 to 10 percent by weight of the composition.

* * * * *